(12) United States Patent
Nakano et al.

(10) Patent No.: US 6,682,909 B2
(45) Date of Patent: Jan. 27, 2004

(54) IMMUNOGENIC COMPOSITION OF HEPATITIS C AND METHODS OF USE THEREOF

(75) Inventors: Eileen T. Nakano, Honolulu, HI (US); David E. Clements, Honolulu, HI (US); Tom Humphreys, Honolulu, HI (US)

(73) Assignee: Hawaii Biotech, Inc., Aiea, HI (US)

( * ) Notice: Subject to any disclaimer, the term of this patent is extended or adjusted under 35 U.S.C. 154(b) by 0 days.

(21) Appl. No.: 09/952,572

(22) Filed: Sep. 13, 2001

(65) Prior Publication Data

US 2002/0119495 A1 Aug. 29, 2002

Related U.S. Application Data

(60) Provisional application No. 60/230,927, filed on Sep. 13, 2000.

(51) Int. Cl.$^7$ .......................... C12P 21/06; C12Q 1/70; C12N 5/00; C07K 16/00; A61K 39/42
(52) U.S. Cl. ................. 435/69.1; 435/5; 435/6; 435/7.1; 435/325; 435/339; 530/388.3; 530/389.4; 530/395; 424/161.1; 424/199.1
(58) Field of Search .................... 435/5, 6, 7.1, 69.1, 435/325, 339; 530/388.3, 389.4, 395; 424/161.1, 199.1

(56) References Cited

U.S. PATENT DOCUMENTS

| | | |
|---|---|---|
| 5,670,152 A | 9/1997 | Weiner et al. |
| 5,670,153 A | 9/1997 | Weiner et al. |
| 5,942,234 A | 8/1999 | Ralston et al. |
| 6,121,020 A | 9/2000 | Selby et al. |

OTHER PUBLICATIONS

Matsuura, Yoshiharu et al., "Processing of E1 and E2 Glycoproteins of Hepatitis C Virus Expressed in Mammalian and Insect Cells," *Virology*, vol. 205, 1994, pp. 141–150.

Saito, Takafumi et al. "Plasmid DNA–Based Immunization for Hepatitis C Virus Structural Proteins: Immune Responses in Mice," Gastroenterology, vol. 112, 1997 pp. 1321–1330.

Spaete, Richard R., "Characterization of the Hepatitis C Virus E2/NS1 Gene Product Expressed in Mammalian Cells," Virology, vol. 188, 1992, pp. 819–830.

Cocquerel, Laurence et al., "A Retention Signal Necessary and Sufficient for Endoplasmic Reticulum Localization Maps to the Transmembrane Domain of Hepatitis C Virus Glycoprotein E2," *Journal of Virology*, Mar. 1998, pp. 2183–2191.

Dubuisson, Jean et al., "Formation and Intracellular Localization of Hepatitis C Virus Envelope Glycoprotein Complexes Expressed by Recombinant Vaccinia and Sindbis Viruses," *Journal of Virology*, Oct. 1994, pp. 6147–6160.

Forns, Xavier et al., "Characterization of Modified Hepatitis C Virus E2 Proteins Expressed on the Cell Surface," *Virology*, vol. 274, pp. 75–85, 2000.

(List continued on next page.)

Primary Examiner—Hankyel T. Park
(74) Attorney, Agent, or Firm—Paradise Patent Services Inc.; George E. Darby

(57) ABSTRACT

The present invention provides truncated HCV E2 polypeptides. The invention HCV E2 polypeptides lack the HVR1 region that provides immune protection against HCV. The present invention also provides immunogenic compositions of such polypeptides and the methods of use thereof.

148 Claims, 6 Drawing Sheets

OTHER PUBLICATIONS

Figure 1A:
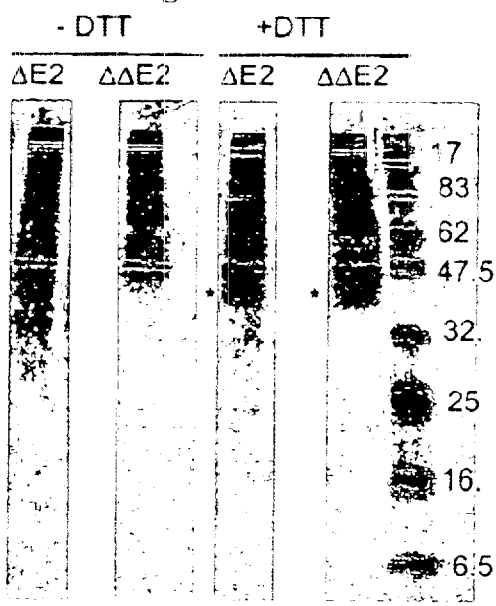
Figure 1B:
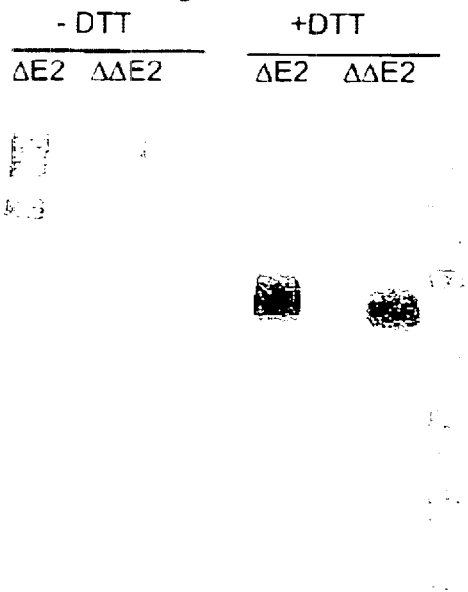
Figure 1C:
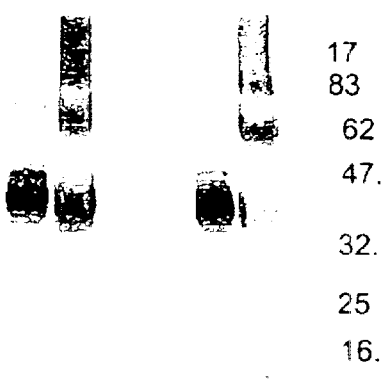

Forns, Xavier et al., "Hepatitis C Virus Lacking the Hypervariable Region 1 of the Second Envelope Protein is Infectious and Causes Acute Resolving or Persistent Infection in Chimpanzees," *PNAS*, Nov. 21, 2000, vol. 97, No. 24, pp. 13318–13323.

Hadlock, Kenneth G. et al., "Human Monoclonal Antibodies that Inhibit Binding of Hepatitis C Virus E2 Protein to CD81 and Recognize Conserved Conformational Epitopes," *Journal of Virology*, Nov. 2000, vol. 74, No. 22, pp. 10407–10416.

Ivey–Hoyle, Mona et al., "Envelope Glycoproteins from Biologically Diverse Isolates of Immunodeficiency Viruses Have Widely Different Affinities for CD4," *Proc. Natl. Acad. Sci. USA*, Jan. 1991, vol. 98, pp. 512–516.

Lanford, Robert E. et al., "Analysis of Hepatitis C Virus Capsid, E1, and E2/NS1 Proteins Expressed in Insect Cells," *Virology*, vol. 197, pp. 225–235, 1993.

Lechner, Sabine et al., "Antibodies Directed to Envelope Proteins of Hepatitis C Virus Outside of Hypervariable Region 1," *Virology*, vol. 243, pp. 313–321, 1998.

Lesniewski, R. et al., "Antibody to Hepatitis C Virus Second Envelope (HCV–E2) Glycoprotein: A New Marker of HCV Infection Closely Associated with Viremia," *Journal of Medical Virology*, vol. 43, pp. 415–422, 1995.

Michalak, Jean–Philippe et al., "Characterization of Truncated Forms of Hepatitis C Virus Glycoproteins," *Journal of General Virology*, vol. 78., pp. 2299–2306, 1997.

Moore, John P. et al., "Characterization of Recombinant gp120 and gp160 from HIV–1: Binding to Monoclonal Antibodies and Soluble CD4," *AIDS*, vol. 4, No. 4, pp. 307–315, 1990.

Nishihara, Tsukasa et al., "Secretion and Purification of Hepatitis C Virus NSI Glycoprotein Produced by Recombinant Baculovirus–Infected Insect Cells," *Gene.*, vol. 129, pp. 207–214, (1993).

Yanagi, Masayuki et al., "Transcripts From a Single Full–Length cDNA Clone of Hepatitis C Virus are Infectious When Directly Transfected into the Liver of a Chimpanzee," *Proc. Natl. Acad. Sci. USA*, vol. 94, pp. 8738–8743, Aug. 1997.

Analysis of expressed ΔE2 and ΔΔE2 in culture medium

Glycosylation Status of Recombinant ΔE2 and ΔΔE2 proteins expressed in Drosophila S2 cells
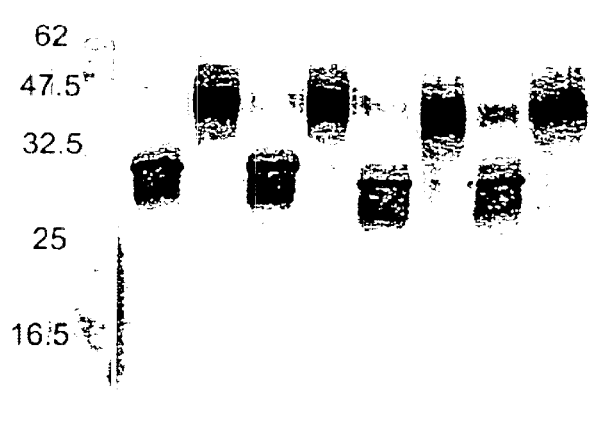
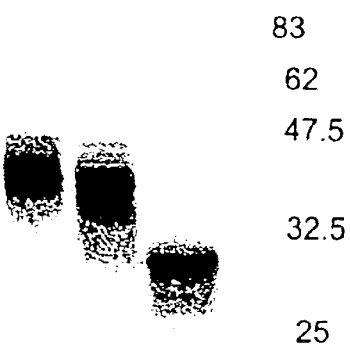
FIG. 2A
FIG. 2B ΔΔE2 protein and purification analysis

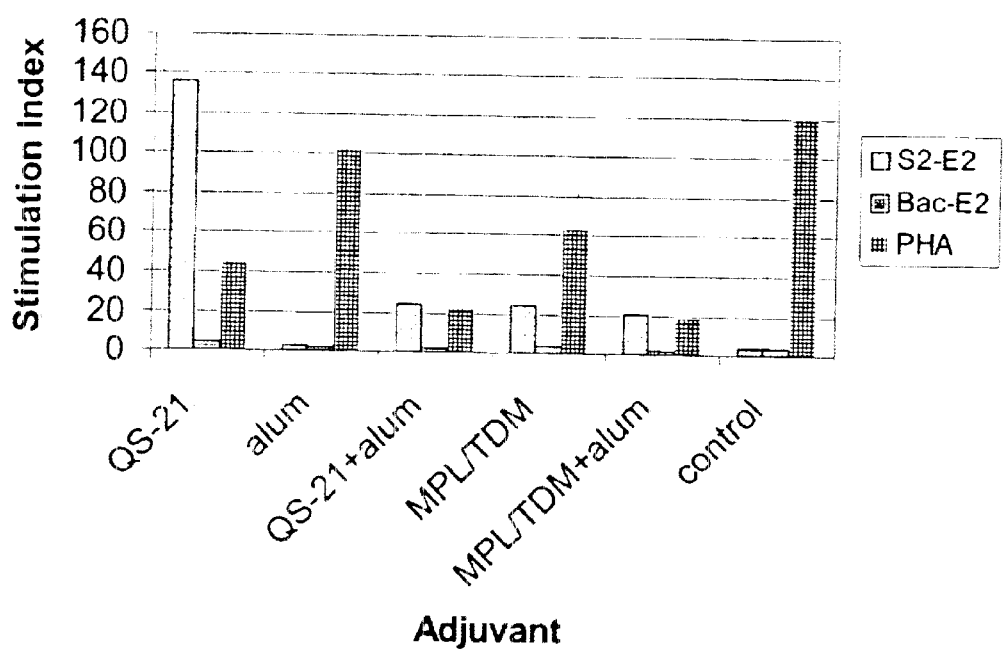
Figure 4: Antigen-specific Tcells are induced in mice immunized with mixtures of antigen and different adjuvants.

Figure 5: Anti-E2 specific antibodies are induced by immunization with antigen/QS21 adjuvant combination.

Fig. 6: cDNA, and amino acid, sequence of HCV ΔΔE2 genotype 1a
(SEQ. I.D. 1 and 8, respectively)

```
CAACTGATCA ACACCAACGG CAGTTGGCAC ATCAATAGCA CGGCCTTGAA  50
 Q  L  I  N  T  N  G  S  W  H  I  N  S  T  A  L  N
TTGCAATGAA AGCCTTAACA CCGGCTGGTT AGCAGGGCTC TTCTATCAAC 100
 C  N  E  S  L  N  T  G  W  L  A  G  L  F  Y  Q  H
ACAAATTCAA CTCTTCAGGC TGTCCTGAGA GGTTGGCCAG CTGCCGACGC 150
 K  F  N  S  S  G  C  P  E  R  L  A  S  C  R  R
CTTACCGATT TTGCCCAGGG CTGGGGTCCT ATCAGTTATG CCAACGGAAG 200
 L  T  D  F  A  Q  G  W  G  P  I  S  Y  A  N  G  S
CGGCCTCGAC GAACGCCCCT ACTGCTGGCA CTACCCTCCA AGACCTTGTG 250
 G  L  D  E  R  P  Y  C  W  H  Y  P  P  R  P  C  G
GCATTGTGCC CGCAAAGAGC GTGTGTGGCC CGGTATATTG CTTCACTCCC 300
 I  V  P  A  K  S  V  C  G  P  V  Y  C  F  T  P
AGCCCCGTGG TGGTGGGAAC GACCGACAGG TCGGGCGCGC CTACCTACAG 350
 S  P  V  V  V  G  T  T  D  R  S  G  A  P  T  Y  S
CTGGGGTGCA AATGATACGG ATGTCTTCGT CCTTAACAAC ACCAGGCCAC 400
 W  G  A  N  D  T  D  V  F  V  L  N  N  T  R  P  P
CGCTGGGCAA TTGGTTCGGT TGTACCTGGA TGAACTCAAC TGGATTCACC 450
 L  G  N  W  F  G  C  T  W  M  N  S  T  G  F  T
AAAGTGTGCG GAGCGCCCCC TTCTGTCATC GGAGGGGTGG GCAACAACAC 500
 K  V  C  G  A  P  P  C  V  I  G  G  V  G  N  N  T
CTTGCTCTGC CCCACTGATT GCTTCCGCAA ACATCCGGAA GCCACATACT 550
 L  L  C  P  T  D  C  F  R  K  H  P  E  A  T  Y  S
CTCGGTGCGG CTCCGGTCCC TGGATTACAC CCAGGTGCAT GGTCGACTAC 600
 R  C  G  S  G  P  W  I  T  P  R  C  M  V  D  Y
CCGTATAGGC TTTGGCACTA TCCTTGTACC ATCAATTACA CCATATTCAA 650
 P  Y  R  L  W  H  Y  P  C  T  I  N  Y  T  I  F  K
AGTCAGGATG TACGTGGGAG GGGTCGAGCA CAGGCTGGAA GCGGCCTGCA 700
 V  R  M  Y  V  G  G  V  E  H  R  L  E  A  A  C  N
ACTGGACGCG GGGCGAACGC TGTGATCTGG AAGACAGGGA CAGGTCCGAG 750
 W  T  R  G  E  R  C  D  L  E  D  R  D  R  S  E
```

IMMUNOGENIC COMPOSITION OF HEPATITIS C AND METHODS OF USE THEREOF

CROSS REFERENCE TO RELATED APPLICATIONS

This application claims priority under 35 U.S.C. 119(e) to U.S. Provisional Application No. 60/230,927, filed on Sep. 13, 2000, which is incorporated herein by reference in its entirety.

FIELD OF THE INVENTION

This invention relates generally to the field of viral proteins and more specifically to variants of hepatitis C having truncated E2 proteins.

BACKGROUND OF THE INVENTION

Hepatitis C Virus (HCV), the etiological agent of post-transfusion and community-acquired non-A, non-B hepatitis is responsible for approximately 20% of all cases of acute hepatitis, 70% of chronic hepatitis and 30% of end-stage liver disease in the United States (Hoofnagle, J. H., Hepatology 26:15S-20S (1997)). Of those chronically infected individuals, 15–30% will develop cirrhosis and 10–30% of these patients will progress to hepatocellular carcinoma and end-stage liver disease. No vaccine is currently available to prevent the disease and treatment options are limited. Development of a safe and efficacious vaccine is hampered by the lack of "correlates of protective immunity", the inability to propagate the virus in culture, and the absence of a small animal model.

Based on its genome structure, hepatitis C virus, has been placed in the family Flaviviridae as a separate genus Hepacivirus. The HCV genome is a single positive-stranded RNA of approximately 9,500 nucleotides containing short 5' and 3' untranslated regions, and a single long open reading frame. The polyprotein is organized in the order, C (core or nucleocapsid), E1 (envelope1), E2 (E2/NS 1, envelope2), P7 (small protein of unknown function), NS2 (nonstructural), NS3, NS4A, NS4B, NS5A, and NS5B. The mature viral proteins are processed from the polyprotein by co- and post-translational proteolytic cleavage by either viral or host cell proteases.

Phylogenic analysis has identified six distinct HCV genotypes (clades) and multiple minor genetic groups. Infection and recovery from disease caused by one virus genotype does not protect from reinfection by homologous or heterologous virus. Infection and recovery, therefore, does not induce protective immunity.

Vaccine development has focused on two viral structural proteins, E1 and E2 (e.g. U.S. Pat. Nos. 5,942,234; 6,121, 020; and 6,150,134). One region of the E2 protein, localized to the N-terminal 30 amino acids (hypervariable region 1 [HVR1]) has been found to be the most heterogeneous region among different virus isolates. Patients with high titer anti-HVR1 antibodies are known to clear the virus, suggesting that there is at least 1 protective epitope within this region, but also suggesting that this region is under direct selective pressure. Anti-HVR1 antibodies are sequence specific, and, therefore, offer no protection from heterologous challenge.

The HCV E2 protein has been shown to bind to the major extracellular loop of CD81, a 25-kDa molecule belonging to the tetraspanin family. The presence of antibodies which inhibit binding to CD81 have been correlated with protection from disease. Epitope mapping studies have suggested that multiple sites within the glycoprotein are responsible for this binding. One epitope lies within the HVR1, while it is clear that a number of others lie outside the HVR1. Monoclonal antibodies isolated from a chronically infected HCV patient were able to inhibit the binding of HCV E2 genotype 1a, 1b, 2a, and 2b recombinant proteins to CD81. These epitopes must lie outside the HVR1 and, therefore, are more conserved across HCV genotypes.

The viral genomic sequence of HCV is known, as are methods for obtaining the sequence. See, e.g., International Publication Nos. WO 89/04669; WO 90/11089; and WO 90/14436. In particular, HCV has a 9.5 kb positive-sense, single-stranded RNA genome and is a member of the Flaviridae family of viruses. Currently, there are 6 distinct, but related genotypes of HCV based on phylogenetic analyses (Simmonds et al., J. Gen. Virol. (1993) 74:2391–2399). The virus encodes a single polyprotein having more than 3000 amino acid residues (Choo et al., Science (1989) 244:359–362; Choo et al., Proc. Natl. Acad. Sci. USA (1991) 88:2451–2455; Han et al., Proc. Natl. Acad. Sci. USA (1991) 88:1711–1715). The polyprotein is processed co- and post-translationally into both structural and non-structural (NS) proteins.

In particular, there are three putative structural proteins, consisting of the N-terminal nucleocapsid protein (termed "core") and two envelope glycoproteins, "E1" (also known as E) and "E2" (also known as E2/NS1). (See, Houghton et al., Hepatology (1991) 14:381–388, for a discussion of HCV proteins, including E1 and E2.) E1 is detected as a 32–35 kDa species and is converted into a single endo H-sensitive band of approximately 18 kDa. By contrast, E2 displays a complex pattern upon immunoprecipitation consistent with the generation of multiple species. The HCV envelope glycoproteins E1 and E2 form a stable complex that is co-immunoprecipitable. The HCV E1 and E2 glycoproteins are of considerable interest because they have been shown to be protective in primate studies.

The envelope of the HCV virion remains uncharacterized. Thus, expression studies using recombinant cDNA templates are the only means currently available to study envelope biosynthesis. E1 and E2 are retained within cells and lack complex carbohydrate when expressed stably or in a transient Vaccinia virus system. Since the E1 and E2 proteins are normally membrane-bound in these expression systems, it would be desirable to produce secreted forms to facilitate purification of the proteins for further use and to produce variants that are antigenic and induce a protective immune response.

SUMMARY OF THE INVENTION

The present invention is based on the seminal discovery that epitopes outside of HVR1 region of HCV E2 protein are sufficient to induce immune response to HCV and provide immune protection against HCV. The invention provides a recombinant cell system that allows the production of recombinant N- and C-terminally truncated Hepatitis C Virus E2 protein in insect cells. Purification of this extracellularly secreted recombinant protein is described herein. Utilization of this recombinant protein for production of an immunogenic response in vivo to purified E2 protein is also provided herein.

In a first embodiment, the invention provides a secreted polypeptide which is a hepatitis C virus (HCV) E2 polypeptide, lacking all or a portion of its membrane spanning domain such that said E2 polypeptide is capable of secretion into growth medium when expressed recombinantly in a host cell, and further comprising a deletion in at least a portion of its N-terminus ending at about amino acid residue 411, numbered with reference to the HCV E2 amino acid sequence (SEQ ID NO:9).

In a preferred aspect, the secreted polypeptide is a hepatitis C virus (HCV) E2 polypeptide, lacking all or a portion of its membrane spanning domain such that said E2 polypeptide is capable of secretion into growth medium when expressed recombinantly in a host cell, wherein said E2 polypeptide lacks at least a portion of its C-terminus beginning at about amino acid residue 662 and at least a portion of its N-terminus ending at about amino acid residue 411, numbered with reference to the HCV E2 amino acid sequence (SEQ ID NO:9). The invention also provides polynucleotides encoding the polypeptides of the invention. An exemplary polynucleotide is set forth in SEQ ID NO:1.

The invention also provides antibodies that specifically bind to a secreted polypeptide which is a hepatitis C virus (HCV) E2 polypeptide, lacking all or a portion of its membrane spanning domain such that said E2 polypeptide is capable of secretion into growth medium when expressed recombinantly in a host cell, and further comprising a deletion in at least a portion of its N-terminus ending at about amino acid residue 411, numbered with reference to the HCV E2 amino acid sequence (SEQ ID NO:9). An exemplary polypeptide is set forth in SEQ ID NO:8.

In another embodiment, the invention provides a method for preparing an immunogenic composition for treatment of HCV. The method includes (a) forming an immunogenic polypeptide composition comprising a polypeptide of the invention, wherein the immunogenic polypeptide composition is suitable for treating HCV; (b) providing a suitable excipient; and (c) mixing the immunogenic composition of (a) with the excipient of (b).

The invention also includes a method of producing anti-HCV antibodies comprising administering to a mammal an effective amount of an immunogenic polypeptide composition comprising a hepatitis C virus (HCV) E2 polypeptide, lacking all or a portion of its membrane spanning domain such that said E2 polypeptide is capable of secretion into growth medium when expressed recombinantly in a host cell, and further comprising a deletion in at least a portion of its N-terminus ending at about amino acid residue 411, numbered with reference to the HCV E2 amino acid sequence (SEQ ID NO:9).

In one embodiment, the present invention provides an immunogenic polypeptide. The immunogenic polypeptide contains an amino acid sequence wherein the amino acid sequence encodes an HCV E2 polypeptide and is not adjacent to an HCV amino acid sequence naturally adjacent to the HCV E2 polypeptide, wherein the HCV E2 polypeptide does not contain hypervariable region 1 of HCV E2 protein and wherein the immunogenic polypeptide provides immune protection against HCV.

In another embodiment, the present invention provides a method of treating HCV infection. The method comprises administering to a subject having or at risk of having HCV (e.g., a recipient of a blood transfusion or a hospital worker), an effective amount of the immunogenic polypeptide of the present invention or the composition thereof.

In still another embodiment, the present invention provides a method of making an HCV E2 immunogenic polypeptide. The method comprises expressing a polynucleotide sequence encoding the HCV E2 immunogenic polypeptide in an insect cell line.

The invention also provides a method of detecting the presence of HCV in a sample comprising contacting the sample with an antibody of the invention and detecting binding of the antibody to the polypeptide, wherein formation of a complex between the antibody and the E2 polypeptide is indicative of the presence of HCV in the sample. Preferably, the antibody is detectably labeled.

BRIEF DESCRIPTION OF THE FIGURES

FIGS. 1A, 1B, and 1C show the analysis of expressed ΔE2 and ΔΔE2 in culture medium. Culture medium from stable S2 cell lines transfected with p78 mttHCVE2AN (genotype 1a), p78 mttHCVE2ΔNΔC (genotype 1a), p85 mttHCV1bE2ΔC (genotype 1b), or p85 mttHCV1bH2ΔNΔC were induced with 200 μM of $CuSO_4$. Cells were pelleted by centrifugation, and the media filtered to remove all traces of cells and debries. Ten microliters of filtered medium was loaded onto an SDS-polyacrylamide gel and the proteins separated by electrophoresis. One gel was stained with Coomassie Brilliant Blue and a second gel electrotransferred to nitrocellulose and probed with monoclonal antibodies A11 and I19.

FIG. 1A shows Coomassie Brilliant Blue stain gel of genotype 1a recombinant proteins.

FIG. 1B shows companion Western Blot of genotype 1a recombinant proteins.

FIG. 1C shows Western blot of genotype 1b recombinant proteins.

FIGS. 2A and 2B show the glycosylation status of recombinant ΔE2 and ΔΔE2 proteins expressed in Drosophila S2 cells. Culture medium from S2 cell lines transfected with plasmids described in FIG. 1 were induced with $CuSO_4$ and harvested after 7 days growth. Media proteins were denatured with SDS and treated with $EndoH_f$ (E), or PNGaseF (P), or no enzyme (−). The samples were loaded onto an SDS polyacrylamide gel and separated via electrophoresis. The gel was electrotransferred onto nitrocellulose and probed with monoclonal antibodies A11 and I19.

FIG. 2A shows the glycosylation status of recombinant proteins from culture medium from two different cell lines expressing ΔE2 and ΔΔE2 protein, treated with or without PNGaseF.

FIG. 2B shows the glycosylation status of recombinant protein from culture medium from a single cell line expressing ΔE2 protein treated with or without $EndoH_f$ or PNGaseF.

FIGS. 3A and 3B show the analysis of ΔΔE2 protein and purification.

FIG. 3A shows silver stained SDS-PAGE.

FIG. 3B shows companion Western Blot probed with anti-E2 antibodies A11 and I19. All lanes represent 1 μg total protein/well. Lane 1: Culture medium; lane 2: proteins eluted from the Phenyl Sepharose column; lane 3: proteins eluted from the *Galanthus Nivalis* lectin column; lane 4: pooled fractions containing ΔΔE2 protein from the sepharcryl 100 column.

FIG. 4 shows antigen-specific T-cells are induced in mice immunized with mixtures of antigen and different adjuvants. Balb/c mice were immunized with formulations containing 10 μg of antigen and different adjuvants as indicated in the figure (see Example 7). Splenocytes of vaccinated mice were restimulated in vitro in the presence of purified S2 derived ΔΔE2 protein or baculovirus derived protein as indicated. Cell proliferation was assessed by measureing [$^3$H] thymidine incorporation. Antigen-specific cell proliferation is expressed by stimulation indices calculated from the incorporated radioactivity in the presence of antigen minus medium blank, divided by the activity incorporated in cells cultured in medium only minus medium blank. Data represents the arithmetic mean of quadruplicate determinations.

FIG. 5 shows anti-E2 specific antibodies were induced by immunization with antigen/QS21 adjuvant combination. Anti-E2 antibody response of animals immunized with ΔΔE2/QS-21 or control animals immunized without antigen to wells coated with E2 isolated from Drosophila S2 cells (S2 E2) or commercially available Baculovirus expressed E2 (Bac E2). Balb/c mice were immunized twice with vaccine containing 10 μg of antigen mixed with different adjuvants (see Example 7). Twelve days following the second immunization the animals were sacrificed and blood collected. The pooled sera were evaluated for anti-E2 antibodies in an indirect ELISA.

FIG. 6 is the cDNA and corresponding amino acid sequence of ΔΔE2 genotype 1a. Yanagi et al, 1997, PNAS 94:8738 describe the cloning of the full length infectious clone of HCV and the accession numbers listed are GenBank AF011751–AF011753 (herein incorporated by reference in their entirety) (see also SEQ ID NO:9 for a representative amino acid sequence). These are three full-length clones that a consensus sequence for H77 was derived.

DESCRIPTION OF THE PREFERRED EMBODIMENTS

The present invention relates in general to immunogenic polypeptides of HCV E2 protein. The invention is based on the discovery that epitopes outside of hypervariable region are sufficient to induce immune response to HCV and provide immune protection against HCV, e.g., multiple HCV genotypes.

By an "E2 polypeptide" is meant a molecule derived from an HCV E2 region. Such a molecule can be physically derived from the region or produced recombinantly or synthetically, based on the known sequence. The mature E2 region of HCV is believed to begin at approximately amino acid 384–385, and end approximately at amino acid 747. The mature E2 protein contains a C-terminal membrane anchor at approximately amino acids 715–730. Further, the mature E2 protein contains a hydrophobic tail region which inhibits efficient folding and secretion of C-terminally truncated recombinant proteins from mammalian cells.

By an "N- and C-terminally truncated E2 polypeptide" is meant a recombinant protein in which N-terminal HVR1 sequences spanning the first 25–30 amino acids and the C-terminal 86 amino acids. Research has demonstrated that recombinant HCV E2 polypeptides devoid of its membrane anchor and hydrophobic tail regions can be secreted into the medium (deletions through amino acids 688, 704 and 715), but that these proteins are incorrectly folded by virtue of recognition by conformationally sensitive monoclonal antibody H2 (Michalak et al. 1997). Furthermore, recombinant E2 ending at 715 was secreted into the medium, but this protein was not recognized by monoclonal antibody H2 and was found in large aggregrates. Expression of a recombinant E2 protein ending in amino acid 664 was efficiently secreted by CHO cells (Lesniewski et al. 1995).

The present invention provides a method to effectively and efficiently produce recombinant HCV E2 proteins for prophylactic and therapeutic purposes. The present applicants have found that recombinantly-engineered amino- and carboxy terminally truncated HCV envelope protein 2, corresponding to amino acids 412–661, is efficiently secreted by an insect cell host, in a form that permits processing to mimic the native conformation of the protein. The efficient secretion of the proteins into the culture medium facilitates purification. Furthermore, the high level of expression permits facile purification of the monomers. In addition, the secreted form is able, especially when administered in the presence of certain modem adjuvants to elicit antibodies and stimulate the production of cytokines from splenocytes of immunized animals. Thus, this protein represents a useful component of a vaccine for protecting subjects against HCV infection.

Truncated E2 protein has been produced using a variety of expression systems including *E. coli* (Mita et al. 1992), *Spodoptera frugiperda* (Chien et al. 1992, Matsuura et al. 1992, Lanford et al. 1993, Nishihara et al. 1993), Chinese Hamster Ovary (CHO e.g. U.S. Pat. No. 5,854,001; Spaete et al. 1992, Harada et al. 1995, Lesniewski et al. 1995, Inudoh et al. 1996), vaccinia (e.g. U.S. Pat. No. 6,245,503) and Sindbis (Ralston et al. 1993, Dubuisson and Rice 1996, Deleersnyder et al. 1997, Michalak et al. 1997). While the expression level of truncated protein has not been reported in most of the above references, expression levels of 6–10 mg/L in CHO cell line has been reported (Lesniewski et al. 1995; Lee et al., 1997). The truncated E2 protein forms multimeric aggregates, and only the monomer appears to be folded correctly and capable of eliciting antibodies which inhibit E2 binding to CD81 (Heile et al. 2000). However, the monomeric fraction represents a minority of the expressed protein. The level of expression of the monomer in this invention is 20–50 mg/L. This level far exceeds that reported for total E2 protein found in the media. This invention, thus, not only seeks to describe a system for the efficient expression of protein, but also an efficient method to purify the monomer.

However, efficient expression and secretion into the media alone does not constitute a viable vaccine; the protein must have native conformation. Traditionally, native conformation was measured by the reactivity of the recombinant protein to patient sera under native (e.g. ELISA) and non-native (Western blot of reduced and denatured recombinant protein). No documentation of the present invention exists in the literature, and, therefore, it was unknown whether it would be recognized by patient serum. Of 43 patient sera evaluated using an ELISA format, 35 recognized the unpurified, recombinant N- and C-terminally truncated HCV E2 protein substantiating that the polypeptide had native conformation. In the same assay, a commercially available recombinant E2 polypeptide was recognized by only two patient sera. However, due to the polyclonal nature of serum, a better judge of native conformation is recognition by conformationally sensitive monoclonal antibodies. Again, the truncated E2 protein described in this invention was recognized by a set of conformationally sensitive monoclonal antibodies, while, the commercial E2 protein was not. The commercial E2 protein was only recognized by conformationally insensitive monoclonal antibodies; these monoclonal antibodies were isolated from animals immunized with reduced and denatured E2 protein (Dubuisson et al. 1994). These two experiments confirm the authenticity of the invention.

Hydrophobicity plots of highly divergent HVR1 sequences are similar and detailed sequence analysis of the region indicates that folding of the HVR1 may be constrained. However, in the context of an infectious cDNA clone, deletion of HVR1 sequences is not lethal, and animals infected with this infectious clone succumb to illness (Forns et al. 2000b). Thus, within virus replication, maturation, and infection, HVR1 sequences are unnecessary if the entire genome is expressed. In addition, expression of a membrane anchored HCV E2 protein devoid of HVR1 sequences is recognized by conformationally sensitive monoclonal antibodies and binds CD81 (Forns et al. 2000a). However, neither of these references teach whether expression of the isolated, secreted E2 protein will result in a correctly folded protein, nor the level of expression within the cell, nor whether the protein will be secreted into the media, nor its stability within culture media.

The uniqueness of the invention is due, in part, to its expression in the Drosophila S2 cell line (U.S. Pat. Nos. 5,550,043; 5,681,713; 5,705,359; 6,046,025). The invention embodied herein makes use of the Drosophila S2 system to produce recombinant HCV N- and C-terminally truncated E2 polypeptide. Despite the fact that an expression system may be reported to be effective for production of one recombinant protein, predictions on efficacy of expression of other recombinant products do not always hold, and, therefore, requires careful evaluation. For example, although the baculovirus expression system has been reported to yield high levels of correctly folded protein, expression of HIV gp120 resulted limited amounts of ill-folded protein (Moore et al. 1990, Murphy et al. 1993), whereas, expression of the same protein in Drosophila S2 cell line resulted in large amounts of well-folded protein (Ivey-Hoyle et al. 1991). Expression of dengue virus envelope protein in Drosophila S2 cell line, again, produced a protein of higher quality as judged by its ability to elicit a potent neutralizing antibody titers, than that produced in the baculovirus expression system (U.S. Pat. No. 6,136,561). Expression of HCV E2 protein in Chinese Hamster Ovary cell line (CHO) but not E2 expressed in yeast or the baculovirus system bound CD81 (Rosa et al. 1996), but dengue envelope protein expressed in CHO cell line was poorly secreted and poorly antigenic compared with that expressed in Drosophila S2 cell line.

Accordingly, the present invention provides immunogenic polypeptides of truncated HCV E2 protein. In one embodiment, the immunogenic polypeptide of the present invention contains an amino acid sequence encoding an HCV E2 polypeptide that does not contain hypervariable region 1 (HVR1). The amino acid sequence encoding the HCV E2 polypeptide of the immunogenic polypeptide of the present invention is not surrounded by or adjacent to an amino acid sequence that naturally surrounds or adjacent to it in HCV.

According to another embodiment of the present invention, the immunogenic polypeptide of the present invention contains an HCV E2 polypeptide with both N-terminal and C-terminal truncations of HCV E2 protein, e.g., does not contain the HVR1 region and the C-terminal region of HCV E2 protein. The mature HCV E2 protein contains a C-terminal membrane spanning region starting from about amino acid 718 and ending at about amino acid 746. The HCV C-terminal hydrophobic tail region in general is from about amino acid 663 to about amino acid 746.

A mature E2 protein is encoded by HCV amino acid sequence starting from about amino acid 384 and ending at about amino acid 746. Hypervariable region 1 (HVR1) is at the N-terminal of HCV E2 protein and is highly variable among HCV isolates. Usually HVR1 contains epitopes that are specific to HCV isolates and induce neutralizing antibodies that are epitope specific, thus provide little protection from infection by HCV of a different HVR1 sequence. In one aspect, the HVR1 region includes the N-terminal amino acids of HCV E2 protein, e.g., from about 384 to 411 amino acids of HCV E2 protein. It should be understood that one of skill in the art could remove a single or multiple amino acid residues as long as the functional features of the polypeptide of the invention are retained, i.e., secreted when produced recombinantly in host cells and immunogenic stimulating a protective immune response in a subject.

In one aspect, the invention truncated E2 polypeptide includes C-terminal amino acids that deletion of which enables the truncated E2 polypeptide to be secreted outside of cell and recognizable by conformation sensitive monoclonal antibody, e.g., H2. In a particular illustrative example, the immunogenic polypeptide of the present invention contains an HCV E2 polypeptide having an amino acid sequence as shown in SEQ ID NO:8.

For purposes of the present invention, the E1 and E2 regions are defined with respect to the amino acid number of the polyprotein encoded by the genome of HCV1, with the initiator methionine being designated position 1. However, it should be noted that the term an an "E2 polypeptide" as used herein is not limited to the HCV1 sequence. In this regard, the corresponding E2 regions in another HCV isolate can be readily determined by aligning sequences from the two isolates in a manner that brings the sequences into maximum alignment. This can be performed with any of a number of computer software packages, such as ALIGN 1.0, available from the University of Virginia, Department of Biochemistry (Attn: Dr. William R. Pearson). See, Pearson et al., Proc. Natl. Acad. Sci. USA (1988) 85:2444–2448.

Furthermore, an "E2 polypeptide" as defined herein is not limited to a polypeptide having the exact sequence depicted in the Figures or Sequence Listing. Indeed, the HCV genome is in a state of constant flux and contains several variable domains which exhibit relatively high degrees of variability between isolates. As will become evident herein, all that is important is that the region which serves to anchor the polypeptide to the endoplasmic reticulum be identified such that the polypeptide can be modified to remove all or part of this sequence for secretion. It is readily apparent that the terms encompass E2 polypeptides from any of the various HCV isolates including isolates having any of the genotypes of HCV described in Simmonds et al., J. Gen. Virol. (1993) 74:2391–2399). Furthermore, the term encompasses any such E2 protein regardless of the method of production, including those proteins recombinantly and synthetically produced.

Additionally, the term "E2 polypeptide" or "truncated E2 polypeptide" encompasses proteins which include additional modifications to the native sequence, such as additional internal deletions, additions and substitutions (generally conservative in nature). These modifications may be deliberate, as through site-directed mutagenesis, or may be accidental, such as through naturally occurring mutational events. All of these modifications are encompassed in the present invention so long as the modified E2 polypeptides function for their intended purpose. Thus, for example, if the E2 polypeptides are to be used in vaccine compositions, the modifications must be such that immunological activity (i.e., the ability to elicit an antibody response to the polypeptide) is not lost. Similarly, if the polypeptides are to be used for diagnostic purposes, such capability must be retained.

An E2 polypeptide "lacking all or a portion of its membrane spanning domain" is an E2 polypeptide, which has been C-terminally truncated to delete all or a part of the membrane anchor sequence which functions to associate the polypeptide to the endoplasmic reticulum. Such a polypeptide is therefore capable of secretion into growth medium in which an organism expressing the protein is cultured. The truncated polypeptide need only lack as much of the membrane anchor sequence as necessary in order to effect secretion. Secretion into growth media is readily determined using a number of detection techniques, including, e.g., polyacrylamide gel electrophoresis and the like and immunological techniques such as immunoprecipitation assays as described in the examples.

Furthermore, the C-terminal truncation can extend beyond the transmembrane spanning domain towards the N-terminus. Thus, for example, E2 truncations occurring at positions lower than, e.g., 411 are also encompassed by the present invention. All that is necessary is that the truncated E2 polypeptides be secreted and remain functional for their intended purpose. However, particularly preferred E2 constructs will be those with C-terminal truncations that do not extend beyond amino acid position 661 and N-terminal truncations that do not extend beyond 411.

A "secreted E2 polypeptide" refers to a truncated E2 protein lacking all or a portion of the membrane spanning domain, as described above.

Two polynucleotides or protein molecules are "substantially homologous" when at least about 40–50%, preferably at least about 70–80%, and most preferably at least about 85–95%, of the nucleotides or amino acids from the molecules match over a defined length of the molecule. As used herein, substantially homologous also refers to molecules having sequences which show identity to the specified nucleic acid or protein molecule. Nucleic acid molecules that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, vols I & II, supra; Nucleic Acid Hybridization, supra.

An "isolated" protein or polypeptide is a protein which is separate and discrete from a whole organism with which the protein is normally associated in nature. Thus, a protein contained in a cell free extract would constitute an "isolated" protein, as would a protein synthetically or recombinantly produced. Likewise, an "isolated" polynucleotide is a nucleic acid molecule separate and discrete from the whole organism with which the sequence is found in nature; or a sequence devoid, in whole or part, of sequences normally associated with it in nature; or a sequence, as it exists in nature, but having heterologous sequences in association therewith.

A "coding sequence" or a sequence which "encodes" a selected protein, is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to cDNA from viral nucleotide sequences as well as synthetic DNA sequences. A transcription termination sequence may be located 3' to the coding sequence.

A "polynucleotide" can include, but is not limited to, viral sequences, procaryotic sequences, viral RNA, eucaryotic mRNA, cDNA from eucaryotic mRNA, genomic DNA sequences from eucaryotic (e.g., mammalian) DNA, and even synthetic DNA sequences.

"Recombinant" as used herein to describe a nucleic acid molecule means a polynucleotide of genomic, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. Recombinant host cells," "host cells," "cells," "cell lines," "cell cultures," and other such terms denoting procaryotic microorganisms or eucaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

The term "subject" as used herein refers to any subject capable of being infected by HCV. Preferably, the subject of the invention is a human. However, as used herein, the term is meant to include humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

According to the present invention, the immunogenic polypeptide of the present invention provides immune protection against HCV. The immune protection against HCV provided by the immunogenic polypeptide can be any immune response, cellular or humoral, that either inhibits or helps to prevent HCV infection. For example, the immunogenic polypeptide of the present invention can bind to CD81, induce antibodies associated with resolving HCV infection, induce production of cytokines, induce antibodies that can neutralize HCV binding to host cells, or prime an immune system against secondary HCV infection or exposure. The immune protection provided by the immunogenic polypeptide of the present invention is preferably protective against more than one HCV genotypes.

The immunogenic polypeptide of the present invention can be a recombinant polypeptide or a synthetic polypeptide. In one embodiment, the immunogenic polypeptide is made in an expression system that preserves or mimics the native conformation of the HCV E2 protein, e.g., recognizable by HCV patient sera under native condition or by conformation sensitive monoclonal antibody. For example, the immunigenic polypeptide of the present invention can be made in a mammalian cell line or an insect cell line, including without limitation, Drosophila S2 cell line. In another embodiment, the immunogenic polypeptide of the present invention is a monomer, e.g., with monomeric expression at a level of 20–50 mg/l. In still another embodiment, the immunogenic polypeptide of the present invention is glycosylated, e.g., at a level similar to the glycosylation obtained in Drosophila S2 cell line.

The present invention also provides an immunogenic composition containing the immunogenic polypeptide of the present invention and an excipient. The compositions of the present invention are useful for treating HCV infection, e.g., by inducing production of neutralizing antibodies. For therapeutic treatment of HCV infection, the compositions of the present invention can be administered alone or in a composition with a suitable pharmaceutical carrier, e.g., water, saline, glycerol, ethanol, etc. The compositions of the present invention can also be administered in combination with other therapeutic agents including, without limitation, immunoregulatory agents, immunoglobulin, cytokines, lymphokines, and chemokines, e.g., IL-2, modified IL-2 (changing cys125 to ser125), GM-CSF, IL-12, gamma-interferon, IP-10, MIP1β, or RANTES.

An effective amount of the compositions to be administered can be determined on a case-by-case basis. Factors should be considered usually include age, body weight, stage of the condition, other disease conditions, duration of the treatment, and the response to the initial treatment. In one embodiment, an effective amount includes an amount of the composition of the present invention that induces an immunological response as measured by 1) the production of antibodies from any of the immunological classes, e.g., immunoglobulins A, D, E, G, or M, 2) the proliferation of B and T lymphocytes, 3) the provision of activation, growth, and differentiation signals to immunological cells, and 4) the expansion of helper T cell, suppressor T cells, and/or cytotoxic T cell and/or gamma-delta-T cell populations.

Typically, the compositions are prepared as an injectable, either as a liquid solution or suspension. However, solid forms suitable for solution in, or suspension in, liquid vehicles prior to injection can also be prepared. The composition can also be formulated into an enteric-coated tablet or gel capsule according to known methods in the art.

The compositions of the present invention may be administered in any way which is medically acceptable which may depend on the disease condition or injury being treated. Possible administration routes include injections, by parenteral routes such as intravascular, intravenous, intraepidural or others, as well as oral, nasal, ophthalmic, rectal, topical, or pulmonary, e.g., by inhalation. The compositions may also be directly applied to tissue surfaces, e.g., during surgery. Sustained release administration is also specifically included in the invention, by such means as depot injections or erodible implants.

According to another feature of the present invention, the immunogenic polypeptide of the present invention can be used as a vaccine to provide immune protection against subsequent HCV infection or exposure. The present invention provides an immunogenic composition or a vaccine comprising the immunogenic polypeptide of the present invention and an adjuvant.

The immunogenic polypeptide of the present invention can be with any suitable adjuvant for stimulating immune response, e.g., providing immune protection. For example, it can be a particulate or a non-particulate adjuvant. A particulate adjuvant usually includes, without limitation, aluminum salts, calcium salts, water-in-oil emulsions, oil-in water emulsion, immune stimulating complexes (ISCOMS) and ISCOM matrices (U.S. Pat. No. 5,679,354), liposomes, nano- and microparticles, proteosomes, virosomes, stearyl tyrosine, and γ-Inulin. A non-particulate adjuvant usually includes, without limitation, muramyl dipeptide (MDP) and derivatives, e.g., treonyl MDP or murametide, non-ionic block copolymers, saponins, e.g., Quil A and QS21, lipid A or its derivative 4' monophosphoryl lipid A (MPL), trehalose dimycolate (TDM), various cytokines including γ-interferon and interleukins 2 or 4, carbohydrate polymers, derivatized polysaccharides, e.g., diethylaminoeytyl dextran, and bacterial toxins, e.g., cholera toxin or *E. coli* labil toxin. In one embodiment, the immunogenic polypeptide of the present invention is used with adjuvant QS-21.

The immunogenic polypeptides of the present invention can also be used with adjuvant formulations that are combinations of various components designed to maximize specific immune responses. For example, in U.S. Pat. No. 6,146,632, the combination of QS21,3-De-O-acylated monophysphoryl lipid A alpha tocopherol, TWEEN 80, and water adjuvant was shown to be the most effective in mediating humoral and cell immunity.

In one embodiment, the immunogenic polypeptide of the present invention is used with other HCV proteins to form a multi-component HCV vaccine for prophylactic or therapeutic treatment of HCV infection. In another embodiment, the vaccine of the present invention is combined with other vaccines including, without limitation other modes of HCV vaccines, e.g., plasmid DNA.

The present invention provides immunoassays for detecting the presence of HCV in a sample containing, or suspected of containing HCV. The immunoassays of the invention can be "sandwich" assays, wherein a second antibody is used to detect specific binding of a first antibody and HCV polypeptides (e.g., SEQ ID NO:8) or can be competition assays, wherein binding of a competitor HCV polypeptide by the "first" antibody is indicative of the presence of HCV in a sample. For example, sera from a subject suspected of containing anti-HCV antibodies can be contacted with a polypeptide of the invention and formation of a complex can be identified, indicating that the subject has been infected with HCV.

The term "antibody" is used broadly herein to include polyclonal and monoclonal antibodies, as well as antigen binding fragments of such antibodies. Depending on the particular method of the invention, antibodies having various specificities can be useful, including an antibody, or antigen binding fragment thereof, that specifically binds a polypeptide of the invention (e.g., SEQ ID NO:8).

The term "specifically binds" or "specifically interacts," when used in reference to an antibody means that an interaction of the antibody and a particular epitope has a dissociation constant of at least about $1\times10^{-6}$, generally at least about $1\times10^{-7}$, usually at least about $1\times10^{-8}$, and particularly at least about $1\times10^{-9}$ or $1\times10^{10}$ or less. As such, Fab, F(ab')$_2$, Fd and Fv fragments of an antibody that retain specific binding activity for an HCV polpeptide of the invention epitope are included within the definition of an antibody. The term "specifically binds" or "specifically interacts" is used similarly herein to refer to the interaction of members of a specific binding pair, as in SEQ ID NO:8 and an antibody.

The term "antibody" as used herein includes naturally occurring antibodies as well as non-naturally occurring antibodies, including, for example, single chain antibodies, chimeric antibodies, bifunctional antibodies and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains (see Huse et al., Science 246:1275–1281, 1989). These and other methods of making, for example, chimeric, humanized, CDR-grafted, single chain, and bifunctional antibodies are well known to those skilled in the art (Winter and Harris, *Immunol. Today* 14:243–246, 1993; Ward et al., *Nature* 341:544–546, 1989; Harlow and Lane, *Antibodies: A laboratory manual* (Cold Spring Harbor Laboratory Press, 1988); Hilyard et al., *Protein Engineering: A practical approach* (IRL Press 1992); Borrabeck, *Antibody Engineering*, 2d ed. (Oxford University Press 1995)). The term "antibody" as used in this invention includes intact molecules as well as fragments thereof, such as Fab, F(ab')2, and Fv which are capable of binding to an epitopic determinant present in an invention polypeptide. Such antibody fragments retain some ability to selectively bind with its antigen or receptor.

An antibody having a desired specificity can be obtained using well known methods. For example, an antibody having substantially the same specific binding activity of H2 can be prepared using methods as described by Liabeuf et al. (supra, 1981) or otherwise known in the art (Harlow and Lane, "Antibodies: A laboratory manual" (Cold Spring Harbor Laboratory Press 1988)).

Where a peptide portion of an HCV polypeptide of the invention used as the immunogen is non-immunogenic, it can be made immunogenic by coupling the hapten to a carrier molecule such as bovine serum albumin (BSA) or keyhole limpet hemocyanin (KLH), or by expressing the peptide portion as a fusion protein. Various other carrier molecules and methods for coupling a hapten to a carrier molecule are well known in the art (see, for example, by Harlow and Lane, supra, 1988). Methods for raising polyclonal antibodies, for example, in a rabbit, goat, mouse or other mammal, are well known in the art (see, for example, Green et al., "Production of Polyclonal Antisera," in *Immunochemical Protocols* (Manson, ed., Humana Press 1992), pages 1–5; Coligan et al., "Production of Polyclonal Antisera in Rabbits, Rats, Mice and Hamsters," in *Curr. Protocols Immunol.* (1992), section 2.4.1).

Monoclonal antibodies also can be obtained using methods that are well known and routine in the art (Kohler and Milstein, *Nature* 256:495, 1975; Coligan et al., supra, 1992, sections 2.5.1–2.6.7; Harlow and Lane, supra, 1988). For example, spleen cells from a mouse immunized with β2-microglobulin, or an epitopic fragment thereof, can be fused to an appropriate myeloma cell line such as SP/02 myeloma cells to produce hybridoma cells. Cloned hybridoma cell lines can be screened using, for example, labeled HCV polypeptide to identify clones that secrete monoclonal antibodies having the appropriate specificity, and hybridomas expressing antibodies having a desirable specificity and affinity can be isolated and utilized as a continuous source of the antibodies. Polyclonal antibodies similarly can be isolated, for example, from serum of an immunized animal. Such antibodies, in addition to being useful for performing a method of the invention, also are useful, for example, for preparing standardized kits. A recombinant phage that expresses, for example, a single chain antibody also provides an antibody that can used for preparing standardized kits.

Monoclonal antibodies, for example, can be isolated and purified from hybridoma cultures by a variety of well established techniques, including, for example, affinity chromatography with Protein-A SEPHAROSE gel, size exclusion chromatography, and ion exchange chromatography (Barnes et al., in *Meth. Mol. Biol.* 10:79–104 (Humana Press 1992); Coligan et al., supra, 1992, see sections 2.7.1–2.7.12 and sections 2.9.1–2.9.3). Methods of in vitro and in vivo multiplication of monoclonal antibodies are well known. For example, multiplication in vitro can be carried out in suitable culture media such as Dulbecco's Modified Eagle Medium or RPMI 1640 medium, optionally replenished by a mammalian serum such as fetal calf serum or trace elements and growth sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo can be carried out by injecting cell clones into mammals histocompatible with the parent cells, for example, syngeneic mice, to cause growth of antibody-producing tumors. Optionally, the animals can be primed with a hydrocarbon, for example, an oil such as pristane (tetramethylpentadecane) prior to injection. After one to three weeks, the desired monoclonal antibody is recovered from the body fluid of the animal.

An antigen binding fragment of an antibody can be prepared by proteolytic hydrolysis of a particular antibody such as H2, or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see, for example, Goldenberg, U.S. Pat. Nos. 4,036,945 and 4,331,647; Nisonhoff et al., *Arch. Biochem. Biophys.* 89:230. 1960; Porter, *Biochem. J.* 73:119, 1959; Edelman et al., *Meth. Enzymol.*, 1:422 (Academic Press 1967); Coligan et al., supra, 1992, see sections 2.8.1–2.8.10 and 2.10.1–2.10.4).

Other methods of cleaving antibodies, such as separation of heavy chains to form monovalent light/heavy chain fragments, further cleavage of fragments, or other enzymatic, chemical, or genetic techniques can also be used, provided the fragments specifically bind to the antigen that is recognized by the intact antibody. For example, Fv fragments comprise an association of variable heavy ($V_H$) chains and variable light ($V_L$) chains, which can be a noncovalent association (Inbar et al., *Proc. Natl. Acad. Sci., USA* 69:2659, 1972). Alternatively, the variable chains can be linked by an intermolecular disulfide bond or cross-linked by chemicals such as glutaraldehyde (Sandhu, *Crit. Rev. Biotechnol.* 12:437, 1992). Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are well known (see, for example, by Whitlow et al., "Methods: A Companion to Methods in Enzymology" 2:97, 1991; Bird et al., *Science* 242:423–426, 1988; Ladner et al., U.S. Pat. No. 4,946,778; Pack et al., *Bio/Technology* 11:1271–1277, 1993; Sandhu, supra, 1992).

Another example of an antigen binding fragment of an antibody is a peptide coding for a single complementarity determining region (CDR). CDR peptides can be obtained by constructing polynucleotides encoding the CDR of an antibody of interest. Such polynucleotides can be prepared, for example, using the polymerase chain reaction to synthesize a variable region encoded by RNA obtained from antibody-producing cells (see, for example, Larrick et al., Methods: A Companion to Methods in Enzymology 2:106, 1991, which is incorporated herein by reference).

The antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA) and the sandwich (immunometric) assay. Detection of the antigens using the antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

Methods of making these fragments are known in the art. (See for example, Harlow and Lane, Antibodies: A Laboratory Manual, Cold Spring Harbor Laboratory, New York (1988), incorporated herein by reference). Monoclonal antibodies are made from antigen containing fragments of the protein by methods well known to those skilled in the art (Kohler & Milstein, Nature 256:495 (1975); Coligan et al., sections 2.5.1–2.6.7; and Harlow et al., Antibodies: A Laboratory Manual, page 726 (Cold Spring Harbor Pub. 1988), which are hereby incorporated by reference. Briefly, monoclonal antibodies can be obtained by injecting mice with a composition comprising an antigen/ligand, verifying the presence of antibody production by analyzing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1–2.7.12 and sections 2.9.1–2.9.3; Barnes et al., "Purification of Immunoglobulin G (IgG)" in Methods In Molecular Biology, Vol. 10, pages 79–104 (Humana Press 1992).

Antibodies that bind to an invention polypeptide can be prepared using an intact polypeptide or fragments containing small peptides of interest as the immunizing antigen (e.g., SEQ ID NO:8). It may also be desirable to produce antibodies that specifically bind to the amino- or carboxyl-terminal domains of an invention polypeptide. For the preparation of polyclonal antibodies, the polypeptide or peptide used to immunize an animal is derived from translated cDNA or chemically synthesized and can be conjugated to a carrier protein, if desired. Commonly used carrier proteins which may be chemically coupled to the immunizing peptide include keyhole limpet hemocyanin (KLH), thyroglobulin, bovine serum albumin (BSA), tetanus toxoid, and the like.

Invention polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See, for example, Coligan, et al., Unit 9, Current Protocols in Immunology, Wiley Interscience, 1994, incorporated herein by reference).

The antibodies of the invention can be bound to many different carriers and used to detect the presence of an antigen comprising the polypeptides of the invention. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or alternatively to the antigen, or will be able to ascertain such, using routine experimentation.

Another feature of the present invention provides a kit containing one or more immunogenic polypeptides of the present invention in a container and an instruction describing the method of using such immunogenic polypeptides. For example, the instruction can describe how to use the immunogenic polypeptide of the present invention or the compositions thereof to treat or immunize a subject for HCV infection. The kit may further comprise an excipient, an adjuvant or a pharmaceutically acceptable carrier.

EXAMPLES

The following examples are intended to illustrate but not to limit the invention in any manner, shape, or form, either explicitly or implicitly. While they are typical of those that might be used, other procedures, methodologies, or techniques known to those skilled in the art may alternatively be used.

Example 1

Preparation of HCV Genotype 1a and 1b 5' and 3' Deleted E2 cDNA Expression Clones To construct the N- and C-terminally truncated HCV E2 protein, the following considerations were made. HCV E2 is a membrane anchored protein, which if expressed as the full-length protein is retained in the endoplasmic reticulum (Cocquerel, L., J Virol 72:2183–91 (1998)). Secreted versions of this glycoprotein required the removal of the hydrophobic anchor domain through at least amino acid 718. However, although recombinant E2 proteins ending at amino acids 688, 704, or 715 are found in the medium only protein ending at amino acid 661 appeared correctly folded by virtue of recognition by conformationally sensitive monoclonal antibody H2 (Michalak, J. P., J Gen Virol 78:2299–306 (1997)). Expression of a recombinant E2 protein ending in amino acid 664 was efficiently secreted by CHO cells (Lesniewski, R., et al., J Med Virol 45:415–22 (1995)). Based on these observations, a cDNA of a recombinant HCV protein ΔΔE2, with its C-terminus at amino acid 661 for genotype 1 a was designed.

The N-terminal approximately 30 amino acids of HCV E2 protein exhibits the highest degree of genetic heterogeneity within the viral genome (HVR1) (Hijikata, M., et al., Biochem Biophys Res Commun 175:220–8 (1991), and Ogata, N., et al., Proc Natl Acad Sci U S A 88:3392–6 (1991)), contains an immunodominant neutralizing epitope which is under direct selective pressure (Kato, N., J Virol 67:3923–30 (1993)), and has been proposed to act as an "immunologic decoy" to target the immune response away from more conserved regions of the molecule (Ray, S. C., et al., J Virol 73:2938–46 (1999)). Deletion of this region, between amino acids 384 and 411, thus, will produce a polypeptide devoid of this "imunologic decoy", capable of guiding the humoral response to conserved epitopes of the protein (Rosa, D., et al., Proc Natl Acad Sci U S A 93:1759–63 (1996); Lechner, S., et al., Virology 243:313–321 (1998); Flint, M., et al., J Virol 73:6235–44 (1999); and Hadlock, K. G., et al., J Virol 74:10407–16 (2000)), thereby providing the opportunity for broader protection against a variety of HCV isolates.

The expression vector constructed to secrete ΔΔE2 recombinant protein (SEQ ID NO. 1) from *Drosophila melanogaster* S2 cells is based on the pMttbns vector (Culp, J. S., et al., Biotechnology (N Y) 9:173–7 (1991)). The vector pMttbns contains a Drosophila metallothionein gene promoter ($P_{Mtt}$), the human tissue plasminogen activator leader sequence ($tPA_L$), and the SV40 early polyadenylation signal (Culp, J. S., et al., Biotechnology (N Y) 9:173–7 (1991)). A 15 bp BamHI DNA fragment containing an XhoI site was deleted from pMttbns to make pMttΔXho, in which the BglII and XhoI restriction endonuclease sites are unique. This change was confirmed by sequence analysis. Ligation into the BglII site fuses the insert to the $tPA_L$ sequence. During normal maturation of tissue plasminogen activator leader sequence the 20 amino acid pre-peptide region of the leader sequence is removed by signalase in the endoplasmic reticulum and the 11 amino acid pro-peptide region is enzymatically removed in the Golgi.

To prepare cDNA of HCV E2 genotype 1a, Polymerase Chain Reaction (PCR) primers 78E2-1575p and 78E2-2324m were used to amplify E2 sequences from plasmid A+5 (obtained from Dr. Robert Purcell, N1H). Plasmid A+5 contains HCV cDNA encoding amino acids 1–882 of genotype 1a cloned into the eukaryotic expression vector pcDNA3.1(Invitrogen). This plasmid was derived from sequences within the infectious cDNA clone of strain H77 (genotype 1a) (Yanagi, M., et al., Virology 244:161–72 (1998)). The number indicates the location of the primer in the reported sequence, and the notation shows whether the oligonucleotide primes the plus (p) or the minus (m) stand synthesis. The sequence of the primers corresponding to HCV cDNA are written in uppercase letters, non-HCV sequences are written in lowercase letters. Two stop codons are placed after the 661th codon of HCV E2.

E2-1575p
BglII
5'-caagatagatctCAACTGATCAACACCAACGGC-3' (SEQ ID NO:2)
78E2-2324m
XbaI
5'-ctactttctaga tta cta CTCGGACCTGTCCCTGTCTTC-3' (SEQ ID NO:3)
end end The PCR conditions were 99° C. for 45 seconds, 60° C. for 1 minute and 70° C. for 2 min for 25 cycles. The PCR products and pMttΔXho vector were digested with Bgl II and Xba I and ligated together under standard conditions. The ligated construct was used to transform *E. coli* strain XL-1 Blue. Individual colonies were picked and the presence of HCV sequences verified by restriction endonuclease digestion. The resulting plasmid, p78 mttHCVE2ΔNΔC, was confirmed by sequence analysis.

The strategy to subclone HCV E2 genotype 1b cDNA followed that described above. Infectious HCV 1b clone (Yanagi et al. 1998) was used as template for this work. PCR primer/adaptors 85E2-1b1491p and 85E2-1b2324m were used to amplify E2 cDNA sequences. As describe above, the expressed protein lacks the membrane anchor and hydrophobic tail. The identity of the resulting plasmid, p85 mttHCV1bE2ΔNΔC was confirmed by sequence analysis.

E2-1b1575p
BglII
5'-caagatagatctCAGCTTGTGAATACCAACGGC3-' (SEQ. ID. NO:4)
85E2-1b2324m
XbaI
5'-ctactttctaga tta cta TTCTGACCTATCCCTGTCCTC-3' (SEQ. ID. NO:5)
end end DNA clones of C-terminally truncated HCV E2 genotype 1a and 1b proteins with an intact N-terminus were constructed using a strategy similar to that described above. The 5' PCR primer/adaptor used for amplification of 1a sequences were 78E2-1491p and the 3' PCR primer/adaptor was 78E2-2324m. The sequence of 78E2-1491p is given below:

78E2-1491p
BglII
5'-attgaaagatctGAAACCCACGTCACCGGGGGAAATG-3' (SEQ. ID. NO:6)

The 5' PCR primer/adaptor used for amplificaton of 1b sequences were 85E2-1b1491p and 85E2-1b2324m. The sequence of 85E2-1b1491p is given below:

85E2-1b1491p
BglII
5'-gttgaaagatctGAGACCCACACGACGGGGAG-3' (SEQ. ID. NO:6)

The resulting plasmids, p78mttHCVE2ΔC and p85 mttHCV1bE2ΔC were confirmed by sequence analysis.

Example 2

Transfection of Drosophila Cells with Expression Plasmids

The Drosophila expression system (U.S. Pat. Nos. 6,046, 025, 5,550,043, 5,705,359, 5,681,713) is based on the cotransfection of S2 cells with the expression plasmid containing the gene of interest and a selection plasmid. Both plasmids integrate at high copy number into the genome. The selection plasmid used in our system, the pCoHygro (van der Staten, A., et al., M. Mol. Cell Bio. 1:1–8 (1989); Glaxo SmithKline; U.S. Pat. No. 5,681,713) encodes the *E. coli* hygromycin B phosphotransferase gene under the transcriptional control of the *D. melanogaster* copia transposable element long terminal repeat and confers resistance to hygromycin B.

*Drosophila melanogaster* Schneider-2 cells (S2; American Type Culture Collection) were plated at $1\times10^6$ cells/ml in 4 ml of Schneiders medium (Invitrogen) supplemented with 10% fetal bovine serum (65° C., 30'; FBS; Hyclone) one day prior to transfection. The cells were transfected with plasmid DNA at a weight ratio of 20:1 using the calcium phosphate coprecipitation method (U.S. Pat. No. 4,634,665; (Wigler, M., et al., Proc Natl Acad Sci U S A 76:1373–6 (1979); Invitrogen). Briefly, 20 μg of expression plasmid (e.g. p78mttHCVE2ΔNΔC) and 1 μg of selection plasmid, pCoHygro, were combined with a calcium solution. This mixture was slowly added to an equal volume of HEPES buffered saline containing phosphate to give a fine calcium phosphate—DNA precipitate. The precipitate was plated onto the S2 cells and incubated overnight. After approximately 16 hours the transfected cells were washed with two changes of medium and replated in 5 ml of fresh Schneiders medium containing 10% FBS. Three days following addition of DNA, 250 µg/ml hygromycin B (Roche Molecular Biochemicals) was added to the cells. All cells were maintained at 26° C. in a humidified chamber. Following significant outgrowth, and adaptation to serum-free medium (IPL-41 medium supplemented with lipids, yeastolate, and Pluronic F68; Invitrogen; 300 µg/ml hygromycin;), transfectants were plated at a cell density of $2 \times 10^6$ cell/ml and induced with 200 mM $CUSO_4$. The media were harvested after 7 days of induction.

Example 3
Characterization of the Secreted HCV ΔE2 and ΔΔE2 Structural Proteins

A. Recombinant HCV ΔE2 and ΔΔE2 of Genotypes 1a and 1b are Found in the Medium.

Stable Drosophila S2 cell line transfectants were induced with 200 µM $CUSO_4$ and grown for seven days at 26° C. Media from induced cultures were harvested, cells pelleted, fluid filtered, and loaded onto a SDS-polyacrylamide gel. The proteins were separated via electrophoresis and electrotransferred to nitrocellulose. The blots were probed with a combination of anti-E2 monoclonal antibodies A11 and I19 (Dubuisson, J., et al., J Virol 70:778–86 (1994)). A clearly visible Coomassie Brilliant Blue staining band for genotype 1b ΔE2 and ΔΔE2 is shown in FIG. 2, suggesting at least 5 µg/ml of recombinant protein can be found in the medium. Comparison of the cell associated recombinant protein and that found in the media suggests that the proteins are efficiently secreted (data not shown). We are not the first to demonstrate secretion of transmembrane anchorless envelope proteins, however, the level of secreted product was surprising in view of literature (Nishihara, T., et al., Gene 129:207–14 (1993)). In view of the fact that this concentration of protein is from a non-clonal population of cells, the amount of secreted protein is much higher than any reported for other stable mammalian cell transfectants.

Figure 3A:
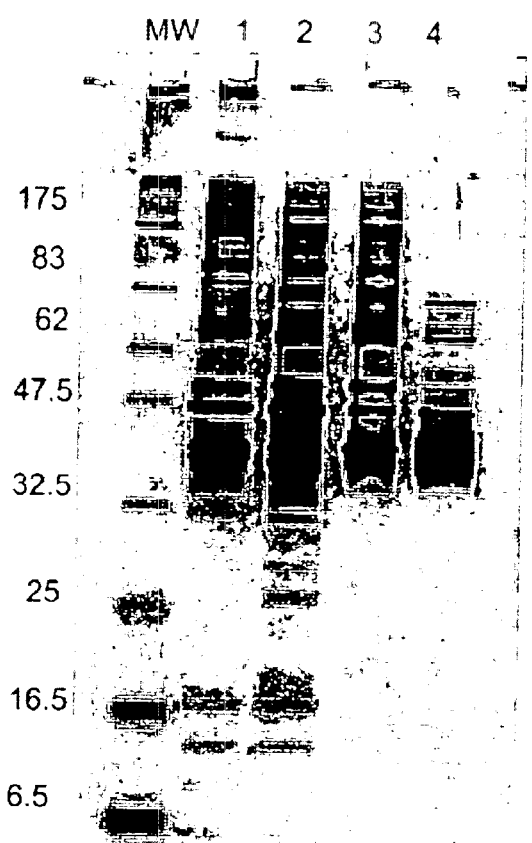
Figure 3B:
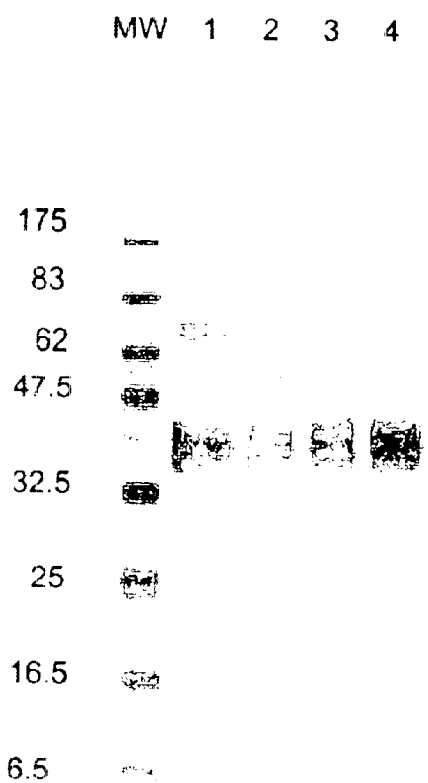

B. Recombinant HCV ΔE2 and ΔΔE2 are glycosylated. HCV E2 contains eleven potential N-linked glycosylation sites. Multiple glycosylation forms of E2 have been described (Lanford, R. E., et al., Virology 197:225–35 (1993)). As shown in FIG. 3, treatment with Endoglycosidase Hf (Endo Hf) and PNGase F (New England Biolabs) demonstrates that both recombinant E2 proteins are glycosylated. Endo Hf cleaves only high mannose and hybrid structures, while PNGase F cleaves all N-glycan chains. A loss of Endo Hf sensitivity has been associated with maturation processing of glycoproteins in mammalian cells, while these glycoproteins remain sensitive to PNGase F digestion. A complex shift was observed for both recombinant E2 proteins (FIG. 3 and data not shown). N-glycosylation systems for Drosophila melanogaster S2 cells have not been reported but those of Spodoptera frugiperda (Sf9) cells have been reported (Hooker, 1999 #15, Inudoh, M., et al., Vaccine 14:1590–6 (1996)). By inference, then, the glycosylation pattern of S2 cells will be less complex compared to mammalian cells, and the presence of high mannose seen in CHO cell expressed E2 proteins probably does not exist. Sf9 cells have been reported to produce proteins with truncated glycans, notably trimannosyl core structures (Kuroda, K., et al. Virology 174:418–29 (1990)) which are resistant to Endo Hf C. Recombinant ΔE2 and ΔΔE2 Genotype 1a proteins are Recognized by HCV Patient Serum.

Forty-three HCV-positive serum samples were obtained from the Hawaii State Department of Health. These samples had tested positive in both the third generation ELISA and RIBA. The infecting genotype was not known for any of these patients, and it is thought that most of these patients have chronic HCV. For the Western blot analysis, culture medium was separated on a 12% SDS-PAGE, and electrotransferred to nitrocellulose. All serum samples were diluted 1:200 in 0.25% BSA in PBS (BPT) and applied to the blot. Bound human-anti-HCV antibodies were detected with alkaline phosphatase conjugated anti-human IgG mouse monoclonal antibody (Sigma) diluted to 1:2000 and nitro-blue-tetrazolium (NBT) and 5-bromo-4-chloro-3-indolyl-phosphate (BCIP, Promega). A sample was judged to be positive if a fuzzy immunoreactive band of appropriate molecular weight could be clearly identified.

Alternatively, an indirect ELISA format was used based on Galanthus nivalis (snow drop) lectin capture (Sigma) to assess the reactivity of the patient serum to native protein. Microtiter wells were coated with the lectin at 5 µg/ml, and buffer-exchanged (PBS) culture medium from induced cultures was added to each well. In addition, a commercially available E2 was tested at 1 µg/ml concentration (baculovirus expressed 70 kD E2, ImmunoDiagnostics, Inc). The wells were blocked with 1% BSA in PBS and the diluted serum (1:500) was added to the wells. Bound antibody was detected using the same mouse anti-human IgG monoclonal antibody diluted to 1:8000 and p-nitro-phenylphosphate. The reaction was read after 30 minutes for recombinant HCV E2 proteins and 60 minutes for the commercially available E2. Media from induced S2 cells transfected with pCoHygro was used as background control. Positive reactivity was determine as any sample with a reading twice the negative serum control background.

As seen in Table 1, the majority of the samples recognized native recombinant E2 protein and not denatured recombinant E2 protein. This would corroborate reports by other researchers that the majority of patient antibodies recognized conformational epitopes (Lanford, R. E., et al., Virology 197:225–35 (1993) and Harada, S., et al., J Gen Virol 76:1223–31 (1995)). We did not test the immunoreactivity of the commercially available E2 in a Western blot format.

In the ELISA format, 34/43 and 35/43 samples recognized ΔE2 and ΔΔE2 recombinant protein respectively (Table 1). The reactivity of the commercially available E2 proteins in the ELISA format was very disappointing. Only two samples could be considered positive. Based on these results and under non-optimal conditions, recombinant proteins ΔE2 or ΔΔE2 represent the best candidates to screen patient sera for anti-HCV envelope antibodies.

The recombinant structural proteins were not recognized by Patients #15, 31, 32, 33, 34, and 44 sera. This is not uncommon, as both chronic and acute patients have been reported to have restricted antibody responses to HCV proteins. In addition, the reactivity of anti-E antibodies has been reported to be genotype specific, and since the infecting genotype is unknown, this could account for the some of the results seen here.

TABLE 1

Immunoreactivity of Patient Sera to Recombinant E2 proteins.

| Native ΔE2 | Denature ΔE2 | Native ΔΔE2 | Denatured ΔΔE2 | Native Bac-E2 |
|---|---|---|---|---|
| 34/43 | 17/43 | 35/43 | 12/43 | 2/43 |

D. Recombinant ΔE2 and ΔΔE2 Genotype 1a Proteins are Recognized by a Panel of Monoclonal Antibodies.

The antigenic properties of the recombinant E2 proteins were investigated by ELISA. Conformationally sensitive and insensitive monoclonal antibodies were used to assess the conformation of the recombinant structural proteins. Using the ELISA format as described above, mouse monoclonal antibody ($1:10^4$–$1:10^5$ dilution) was added in place of the human serum and bound antibody was detected using alkaline phosphatase conjugated polyclonal anti-mouse (H+L) antibody (Caltag) and p-nitro phenylphosphate. Again the commercially available baculovirus system expressed HCV E2 protein served as a control. Table 2. describes the immunoreactivity observed. Specificities for the individual monoclonal antibodies are described in the table. All of the monoclonal antibodies, conformationally sensitive (H2, H53, CBH4D, CBH4G, and CBH7) or conformationally insensitive (A11, 119, and MO12) bound captured recombinant ΔE2 or ΔΔE2 genotype 1a protein. The commercially available baculovirus E2 was not recognized by H2, H53, or the human conformationally sensitive monoclonal antibodies. Interestingly the baculovirus E2 was not recognized by monoclonal antibody 119, a monoclonal antibody which performs very well in Western blot formats. This result demonstrates that the deletion of the HVR1 does not alter epitopes recognized by this panel of antibodies, suggesting that the shape of the N- and C-terminally truncated protein and the C-terminally truncated protein are similar.

TABLE 2

Immunoreactivity of recombinant HCV proteins.

| monoclonal antibody | Specificity | Reactivity | | |
|---|---|---|---|---|
| | | crude ΔE2 | crude ΔΔE2 | baculovirus expressed E2 |
| A11[a] | non-conformational | yes | yes | yes |
| I19[a] | non-conformational | yes | yes | no |
| MO12[b] | non-conformational | yes | yes | yes |
| H2[a] | conformational | yes | yes | no |
| H53[a] | conformational | yes | yes | no |
| CBH-4D[c] | conformational non-NOB | yes | yes | no |
| CBH-4G[c] | conformational non-NOB | yes | yes | no |
| CBH-7[c] | conformational NOB | yes | yes | no |

[a] = mouse anti-HCV E2 monoclonal antibodies (Dubuisson, J., et al., J Virol 68:6147-60)
[b] = rat anti-HCV E2 monoclonal antibody (Inudoh, M., et al., Microbol Immunol 42:875-7 (1998))
[c] = human anti-HCV E2 monoclonal antibodies (Hadlock, K., et al., J Virol 74:10407-16 (2000))

Example 4
Subcloning of Transfected S2 Cells by Limiting Dilution

Immunofluorescence analysis of transfected bulk culture cells expressing ΔΔE2 protein indicated that no more than 5% of the bulk culture was positive for the expression of recombinant protein. Obtaining a pure population of antigen expressing cells (subcloning), Therefore, should increase the total amount of secreted protein.

Subcloning these transfectants was accomplished by plating the cells in 96 well plates at the following densities, 150 cells/well, 100 cells/well, 50 cells/well and 25 cells/well. The cells were resuspended in media containing the following components: ⅓ 5–7 day conditioned media; ⅓ IPL-41 (Invitrogen/Gibco) supplemented with yeastolate and 20% Fetal Bovine Serum; ⅓ fully supplemented IPL-41. Wells were fed every five-seven days. At the first feeding, 100 µl of plating medium was added. Thereafter, 100 µl of medium was remove from each well and 100 µl of supplimented IPL-41 was added. When significant outgrowth had occurred, approximately 25 µl of cells was transferred to wells containing 200 µl of supplimented IPL-41 containing 200 µM $CuSO_4$. Following one week induction, the media was harvested and expression was analyzed by standard dot blot techniques probing with anti-HCV E2 monoclonal antibody H53 (Cocquerel, L., et al., J Virol 72:2183–91 (1998)). The best expressors were then expanded and evaluated in under standard induction conditions. Media proteins were separated by SDS-PAGE and electrotransferred to nitrocellulose, and probed with anti-E2 monoclonal antibodies as described in Example 3.

Contrary to intuition, wells plated at lower cell density did not always result in subclones expressing a greater amount of recombinant protein. The subclone which expressed the greatest amount of protein was identified from a 50 cell/well plating. We estimate that this subclone expresses approximately 50–100 mg/L of recombinant ΔΔE2 protein.

Example 5
Purification of HCV ΔΔE2 1a Antigen

Purification of monomeric ΔΔE2 protein was accomplished in three steps. One goal of the purification procedure was to separate disulfide bonded multimeric, aggregated E2 protein from the monomeric recombinant protein as it has been reported that only monomeric E2 protein binds CD81 (Heile, J. M., et al., J Virol 74:6885–92 (2000)), and therefore, only the monomer presents protective epitopes. Due to this requirement, a large proportion of the total expressed E2 protein was discarded during the purification process.

*Drosophila melanogaster* Schneider-2 cells transfected with plasmid p78 mttHCVE2ΔNΔC, subclone 8E were cultured in spinner flasks at $1 \times 10^6$ cells/ml and induced for 5 days with 0.5 mM $CUSO_4$. Three hundred milliliters of harvested media (total protein concentration of 630 µg/ml) was mixed with 300 ml of 2 M sodium sulfate (Aldrich) in 20 mM sodium phosphate pH 6.5 (Dibasic sodium phosphate, Fisher; Monobasic sodium phosphate, Sigma). The 1 M sodium sulfate mixture was put through a 0.45 µm Nalgene filter (Nalge Nunc).

ΔΔE2 1a protein was captured and concentrated using a 5 ml packed Phenyl Sepharose high performance matrix column (Pharmacia Biotech). To prepare the column, 10 bed volumes of distilled water, followed by 5 bed volumes of 0.5 M sodium sulfate-20 mM sodium phosphate pH 6.5, and finally 1 M sodium sulfate-20 mM sodium phosphate pH 6.5 at a flow rate of 2 ml/min was used to wash the column. The column was loaded with 600 mls of the 1 M sodium sulfate-20 mM sodium phosphate pH 6.5 filtered mixture, washed with 6 bed volumes of 1 M sodium sulfate-20 mM sodium phosphate pH 6.5, and finally protein was eluted with 10 bed volumes of 20 mM sodium phosphate pH 6.5. The total protein concentration was 900 µg/ml in 50 mls which was a 1.4 fold purification.

The eluted fraction as next loaded onto a *Galanthus Nivalis* lectin column (cross linked to 4% agarose; Sigma).

This column was chosen based on the glycosylation status of ΔΔE2 1a. Ten milliliters of the eluted fraction from the phenyl sepharose column was incubated with 3.5 ml lectin (packed volume) for 1 hour at room temperature. The mixture was poured into a column, flow through collected, and the column was washed with 4 bed volumes of phosphate buffered saline (PBS) at a flow rate of 1 ml/min. ΔΔE2 1a was eluted with 1 M methyl α-D-mannopyranoside (Sigma) in PBS. The total protein concentration was 130 μg/ml in 15 ml which contained about 50% pure ΔΔE2 1a (FIG. 4).

In the final purification step, 12 mls of the lectin purified ΔΔE2 1a was concentrated to 1 ml using a Centriplus 10,000 MW filter (Millipore), and loaded on a Sephacryl S-100HR column (Sigma), which had been equilibrated with PBS. The column size had a total volume of $V_T$=173 ml and a void volume of $V_o$=61 ml. A pump was added to produce a flow rate of 0.5 ml/min, and fractions were collected following flowed through of approximately 60 ml of PBS. Six hundred microliter fractions were taken and analyzed by SDS-PAGE and Western blot analysis. Fractions containing ΔΔE2 1a monomer were pooled and concentrated through a Centricon 10,000 MW filter (Millipore). The total protein concentration was 150 μg/ml, which contained 80% pure ΔΔE2 1a.

As can be seen in FIG. 4, the purified recombinant E2 fraction does not contain multimeric aggregates of the E2 protein.

Example 6
Purified HCV ΔΔE2 Genotype 1a Protein is Recognized by a Panel of Monoclonal Antibodies To assess whether the recombinant N- and C-terminally truncated E2 protein had retained its native conformation following purification, its immunoreactivity with anti-HCV E2 monoclonal antibodies was analyzed in an indirect ELISA (Dubuisson, J., et al., J Virol 68:6147–60 (1994); Deleersnyder, V., et al., J Virol 71:697–704 (1997); Cocquerel, L., et al., J Virol 72:2183–91 (1998); Inudoh, M., et al., Microbiol Immunol 42:875–7 (1998); and Hadlock, K., et al., J Virol 74:10407–16 (2000)). The results of this assay are presented in Table 3 below. Specificities for the individual monoclonal antibodies are described in the table. Significantly, the recombinant protein was recognized by the conformationally sensitive monoclonal antibodies, while the baculovirus expressed E2 protein was not, confirming the results of sandwich ELISA presented in Example 3 above. Hadlock et al. (2000) have determined whether their human monoclonal antibodies block the binding of E2 to CD81, thus, the fact that human monoclonal CBH-7, a monoclonal antibody which blocks E2 binding to CD81 (an NOB monoclonal antibody), is notable, as it implies that the recombinant protein presents a critical protective epitope.

The indirect ELISA protocol is presented below:

1) Microtiter plate wells (96-well Immulon 2 plates, Dynex Technologies, Inc.) were coated with 75 μl of coating antigens S2-expressed HCV E2 or Baculovirus expressed HCV E2 (ImmunoDiagnostics, Inc.) at 15 μg/ml in phosphate-buffered saline (PBS), overnight at 4° C.

2) Coating antigen solutions were discarded and 75 μl of 10-fold serial dilutions (starting at 1:500) of the mouse monoclonal antibody in PBS containing 0.05% Tween-20 detergent and 0.1% bovine serum albumin (PBST/BSA). The plates were incubated at room temperature for 2 hours.

The sera was discarded from the plates and the wells washed 3 times with PBS containing 0.05% Tween-20 detergent (PBST).

4) 75 μl of Goat anti-Mouse IgG alkaline phosphatase conjugate (Southern Biotechnology Associates) diluted 1:2,000 in PBST/BSA was then added to each well and the plates incubated for 1 hour at room temperature.

5) The Goat anti-Mouse IgG alkaline phosphatase conjugate was discarded and the wells washed 4 times with PBST.

6) 100 microliters of p-nitrophenylphosphate (pNPP; Sigma Chemical Co.) at 1 mg/ml in a buffer consisting of 100 mM Tris-HCl; 100 mM NaCl, 5 mM $MgCl_2$, pH 9.5 was then added to each well and the plates were incubated at room temperature for 30 minutes.

7) 50 μl of 2.5 N NaOH was then added to each well to stop the reaction.

8) The absorbance at 405 nm of the solution in each well was then determined using an automated microplate reader (spectrophotometer).

9) Reactions were deemed positive it the absorbance values at 405 nm were greater than two fold above the background control absorbance.

TABLE 3

Immune reactivity of various anti-HCV E2 monoclonal antibodies with the purified, recombinant ΔΔE2 protein and baculovirus expressed E2.

| monoclonal antibody | Specificity | Reactivity purified ΔΔE2 1a | Reactivity baculovirus expressed E2 |
|---|---|---|---|
| A11[a] | non-conformational | yes | yes |
| I19[a] | non-conformational | yes | yes |
| MO12[b] | non-conformational | yes | yes |
| H2[a] | Conformational | yes | no |
| H53[a] | Conformational | yes | no |
| CBH-4D[c] | Conformational non-NOB | yes | no |
| CBH-4G[c] | Conformational non-NOB | yes | no |
| CBH-7[c] | Conformational NOB | yes | no |

[a]= mouse anti-HCV E2 monoclonal antibodies (Dubuisson, J., et al., J Virol 68:6147-60 (1994); Deleersnyder, V., et al., J Virol 71:697-704 (1997); and Cocquerel, L., et al., J Virol 72:2183-91 (1998))
[b]= rat anti-HCV E2 monoclonal antibody (Inudoh, M., et al., Microbiol Immunol 42:875-7 (1998))
[c]= human anti-HCV E2 monoclonal antibodies (Hadlock, K., et al., J Virol 74:10407-16 (2000))

Example 7
Immunization of Mice with Purified HCV ΔΔE2 Protein

Six groups of five 8 week old, female, Balb/c mice (Simonsen Laboratories) each were immunized with purified ΔΔE2 1a protein in a variety of modem and traditional adjuvants. All animals were given a primary vaccination, followed three weeks later by a booster vaccination with identical antigen/adjuvant combinations by the same route. Spleens were harvested four and seven days following the second immunization for analysis of cellular immune responses, and sera was taken twelve days following the second immunization for determination of antigen specific antibody response. The following adjuvants were evaluated: alum (Pierce Chemical Co.), QS-21 (Antigenics/Aquila Biopharmaceuticals), MPL-TDM (Corixia Corp.), QS-21+alum, MPL/TDM+alum.

Group 1:10 μg of HCV ΔΔE2/10 μg of adjuvant QS-21 in 0.2 ml, administered subcutaneously;

Group 2: 10 μg of HCV ΔΔE2/2.25 mg alum (AlO(OH)+Mg(OH)$_2$; in 0.2 ml, administered subcutaneously;

Group 3: 10 μg of HCV ΔΔE2/10 μg QS-21+2.25 mg alum in 0.2 ml, administered subcutaneously;

Group 4: 10 μg of HCV ΔΔE2/[50 μg Monophosphoryl Lipid A (MPL)/50 μg Synthetic Trehalose Dicorynomycolate (TDM) in 0.2 ml, administered intraperitoneally;

Group 5: 10 μg of HCV ΔΔE2/(50 μg MPL/50 μg TDM+ 2.25 mg alum) in 0.2 ml, administered intraperitoneally;

Group 6: 10 μg QS-21+2.25 mg alum in 0.2 ml, administered subcutaneously.

Preparation of antigen/adjuvant mixtures [all solutions/suspensions were made in phosphate-buffered saline (PBS), pH 7]:

1) equal volumes of QS-21 (100 μg/ml) and ΔΔE2 (100 μg/ml) were mixed together;
2) an equal volume of alum (22.5 mg/ml in the form of a slurry) was added dropwise to an equal volume of ΔΔE2 (100 μg/ml) while continuously swirling, followed by mixing for 30 min. at room temp.;
3) one half volume of QS-21 (200 μg/ml) was mixed with one volume of ΔΔE2 (100 μg/ml), followed by addition of one half volume of alum (45 mg/ml in the form of a slurry) dropwise while continuously swirling, followed by mixing for 30 min. at room temp.;
4) MPL/TDM (in dry form) was reconstituted at a concentration of 0.5 mg each/ml in PBS by vigorous vortex mixing, as directed by the manufacturer's instructions, followed by addition of an equal volume of ΔΔE2 (100 μg/ml) and further vortex mixing;
5) MPL/TDM (in dry form) was reconstituted at a concentration of 1.0 mg each/ml in PBS by vigorous vortex mixing, as directed by the manufacturer's instructions, followed by addition of two volumes of ΔΔE2 (100 μg/ml) with further vortex mixing, followed by addition of one volume of alum (45 mg/ml in the form of a slurry) dropwise while continuously swirling, followed by mixing for 30 min. at room temp.;
6) one volume of alum (22.5 mg/ml in the form of a slurry) was added to one volume of QS-21 (100 μg/ml) dropwise while continuously swirling followed by mixing for 30 min. at room temp.

Example 8
Preparation of Mouse Spleen Cell Suspensions for the Evaluation of the Cellular Immune Response to Purified HCV ΔΔE2 Protein One mouse from each group listed under Example 7 above was sacrificed on the seventh day post vaccination. Splenectomies were performed and splenocyte suspensions were prepared from each spleen in cell culture medium (RPMI 1640 supplemented with 10% heat-inactivated fetal bovine serum, 2 mM L-glutamine, 50 units of penicillin/ml, 50 μg streptomycin/ml, and 50 μg gentamicin/ml). Membraneous debris were allowed to settle out and the cell suspension aspirated and centrifuged. The supernatant was discarded and the cell pellet resuspended in an erythrocyte lysis solution composed of 0.15 M $NH_4Cl$, 10 mM $NaHCO_3$, 0.1 mM EDTA, pH 7.3 (previously filter sterilized). The cell suspension in lysis solution was allowed to remain at room temp. for 10 min. and then centrifuged. The supernatant was discarded and the cell pellet resuspended in supplemented cell culture medium as above. Cell counts were performed on each suspension using a hemacytometer, and diluted to $4 \times 10^6$ cells/ml with culture medium.

Example 9
Evaluation of T-Cell Proliferation in Mice Immunized with Purified HCV ΔΔE2 Protein Using Several Different Adjuvants Aliquots (0.1 ml) of each cell suspension prepared in Example 8 above were dispensed into wells of a 96-well cell culture plate. Aliquots (0.1 ml) of the stimulants listed below were then dispensed into wells containing each of the cell suspensions (in quadruplicate). Cultures were then incubated at 37° C./5% $CO_2$/humidified for specified times (3 days for mitogenic stimulation, 7 days for stimulation with recall antigens). One microcurie of [$^3$H]thymidine was then added to each well (in a volume of 0.01 ml), and incubation continued for 18 hrs. After that period of time, the cell cultures were harvested onto a glass fiber filtration plate and washed extensively using a vacuum driven harvester system (Filtermate Plate Harvester, Packard Instrument Co.). The filtration plate was then analyzed for radioactivity using the TopCount Microplate Scintillation and Luminescence Counter (Packard Instrument Co.). The following stimulants were used: a) HCV E2, expressed in Drosophila S2 cells as described above; b) HCV E2, Baculovirus expressed (ImmunoDiagnostics, Inc.), c) *Phaseolus vulgaris* lectin (phytohemagglutinin (PHA), a T cell mitogenic stimulant; Sigma Chemical Co.), d) no stimulant (cell control; culture medium only plus cells). S2 expressed ΔΔE2 was used at 5 μg/ml and PHA at 10 μg/ml (final concentrations). The results of these assays are shown in FIG. 5, and demonstrate that Drosophila S2 cell expressed HCV E2 was effective in in vitro stimulation of immune splenocytes from mice vaccinated with HCV E2 in association with some, but not all of the adjuvants tested. The adjuvants that were the most efficacious in engendering splenocytes capable of responding to in vitro stimulation were QS-21 and MPL/TDM. Alum proved to be ineffective for this purpose. Addition of alum to the QS-21 adjuvanted antigen mixture seemed to depress the stimulation of immune splenocytes, while the addition of alum to MPL/TDM had less of an effect. The Baculovirus expressed HCV E2 protein did not stimulate these immune splenocytes to any significant extent, suggesting that this protein did not contain the appropriate configuration of epitopes required for recognition by the responding immune lymphocyte population.

Example 10
Evaluation of the Cytokine Response of Purified HCV E2 protein in Mice Using Several Different Adjuvants Aliquots (0.4 ml) of each cell suspension prepared in Example 8 above were dispensed into wells of a 24-well cell culture plate. Aliquots (0.4 ml) of the stimulants listed below were then dispensed into wells containing each of the cell suspensions. Cultures were then incubated for 5 days at 37° C./5% $CO_2$/humidified. The culture supernatants were then harvested and frozen for analysis for specific cytokines at a later date. The cytokines interferon-gamma (IFN-gamma) and interleukin-4 (IL-4) were assayed by an enzyme-linked immunosorbent assay (ELISA) technique as follows.

1) Microtiter plate wells (96-well Immulon 2 plates, Dynex Technologies, Inc.) were coated with 75 μl each of capture antibodies (anti-mouse IFN-gamma or anti-mouse IL-4; BD Pharmingen Research Products) at 5 μg/ml in phosphate-buffered saline (PBS), overnight at 4° C.
2) Coating antibody solutions were discarded and 200 μl of culture medium (RPMI 1640; Sigma Chemical Co.) containing 10% fetal bovine serum (FBS; Sigma Chemical Co.) were added to each well and the plates incubated at room temperature for 1 hr.
3) The RPMI 1640+10% FBS (blocking solution) was then discarded and the wells washed 3 times with PBS containing 0.05% Tween 20 detergent (PBST).

4) 75 μl of culture supernatants or standards of IFN-gamma (varying from 1–10 ng/ml) or IL-4 (varying from 0.25–5 ng/ml) diluted in RPMI 1640/10% FBS were then added to designated wells on the microtiter plates and the plates incubated at room temperature for 2 hrs.

5) The culture supernatants or standards were then discarded and the wells washed 3 times with PBST.

6) 75 μl of detection antibodies (biotinylated anti-mouse IFN-gamma or biotinylated anti-mouse IL-4; BD Pharmingen Research Products) at 2 μg/ml in PBST containing 0.1% bovine serum albumin (PBST/BSA) were then added to the appropriate wells on the microtiter plates and the plates incubated at room temperature for 2 hrs., or overnight at 4° C.

7) The detection antibodies were then discarded and the wells washed 3 times with PBST.

8) 75 μl of streptavidin-alkaline phosphatase conjugate (Southern Biotechnology Associates), diluted 1:2000 in PBST/BSA, was then added to each well and the plates incubated at room temperature for 1 hr. or overnight at 4° C.

9) The streptavidin-alkaline phosphatase was then discarded and the wells washed 4 times with PBST.

10) 100 μl of p-nitrophenylphosphate (pNPP; Sigma Chemical Co.) at 1 mg/ml in a buffer consisting of 100 mM Tris-HCl, 100 mM NaCl, 5 mM $MgCl_2$, pH 9.5, were then added to each well and the plates incubated at room temperature in the dark for 15 min.

11) 50 μl of 2.5 N NaOH were then added to each well to stop the reaction.

12) The absorbance at 405 nm of the solution in each well was then determined using an automated microplate reader (spectrophotometer).

13) The absorbance values obtained from the IFN-gamma and IL-4 standards were used to establish a "standard curve" for each of these cytokines. The absorbance values obtained from the culture supernatant samples were then used to assign values of cytokine concentration to each sample by interpolation of the standard curves.

The results of these assays are shown in Tables 4 and 5, and indicate that the Drosophila S2 cell expressed HCV ΔΔE2 was capable of stimulating immune splenocytes to produce the cytokines IFN-gamma and IL-4 in vitro, if the splenocytes were taken from mice vaccinated with the S2 cell expressed E2 in association with the adjuvant QS-21. The splenocytes taken from mice vaccinated with S2 cell expressed ΔΔE2 using alum or MPL+TDM as adjuvants did not produce these cytokines when stimulated in vitro. Again, the Baculovirus expressed E2 did not stimulate any of the immune splenocyte populations, including the QS-21 adjuvanted population, to produce cytokines in vitro, consistent with Example 10 above.

TABLE 4

Effect of Different Antigen/Adjuvant Combinations on the Release of Interleukin-4.

| | Adjuvant/Antigen Combination | | | | | |
|---|---|---|---|---|---|---|
| Stimulant | QS-21 | Alum | QS-21 + Alum | MPL/ TDM | MPL/TDM + Alum | Control |
| S2-E2 | 0.59 | 0 | 0.064 | 0 | 0.069 | 0 |
| Bac-E2 | 0 | 0 | 0 | 0 | 0 | 0 |

TABLE 4-continued

Effect of Different Antigen/Adjuvant Combinations on the Release of Interleukin-4.

| | Adjuvant/Antigen Combination | | | | | |
|---|---|---|---|---|---|---|
| Stimulant | QS-21 | Alum | QS-21 + Alum | MPL/ TDM | MPL/TDM + Alum | Control |
| PWM | 0.47 | 0.37 | 0.42 | 0.78 | 1.7 | 0.93 |
| Unstim | 0 | 0 | 0 | 0 | 0 | 0 |

Table 4.

Balb/c mice were immunized and boosted as described in Example 7. Spleens were harvested 7 days after the second immunization. Splenocytes were cultured in the presence of stimulant and supernatants harvested 5 days later. Results are presented as the concentration of IL-4 in ng/ml.

TABLE 5

Effect of Different Antigen/Adjuvant Combinations on the Release of Interferon-gamma.

| | Adjuvant/Antigen Combination | | | | | |
|---|---|---|---|---|---|---|
| Stimulant | QS-21 | Alum | QS-21 + Alum | MPL/ TDM | MPL/TDM + Alum | Control |
| S2-E2 | 1.7 | 0 | 0.31 | 0 | 0.069 | 0 |
| Bac-E2 | 0 | 0 | 0 | 0 | 0 | 0 |
| PWM | 0.57 | 0 | 0.77 | 0.76 | 4 | 1 |
| Unstim | 0 | 0 | 0 | 0 | 0 | 0 |

Table 5.

Spleens of immunized Balb/c mice were harvested, and immune splenocytes stimulated with different antigens as described in the table. Results are given as the concentration of INF-γ in ng/ml.

Example 11

Evaluation of the Humoral Immune Response of Purified ΔHCV E2 Protein in Mice Using Several Different Adjuvants Twelve days after the booster immunization as described in Example 7 above, three mice from each group were bled and serum obtained. Serum samples were pooled from the mice in each group. Sera were analyzed for antibody (IgG) to purified HCV ΔΔE2 protein by an enzyme-linked immunosorbent assay (ELISA) technique as described in Example 6. Pooled sera from immunized mice were serially diluted in PBST/BSA and added to Drosophila S2 cell expressed HCV ΔΔE2 or commercially available Baculovirus expressed E2 and blocked wells. Signal was generated by the addition of goat anti-mouse-alkaline phosphatase conjugate and p-nitrophenylphosphate. Absorbance values at 405 nm were graphed against the log of the antiserum dilution and a titering curve constructed among the data antiserum points for each mouse group. The titer was determined from these titering curves to be the serum dilution which produced an absorbance of 0.5 at 405 nm.

The antibody titrations for the serum sample obtained from mice vaccinated with the recombinant soluble ΔΔE2/QS-21 adjuvant combination are depicted in FIG. 6. The antibody titers obtained from this sample were 1:112 against the Drosophila S2 cell expressed ΔΔE2 and 1:22 against the Baculovirus expressed E2. This result suggests that while the antibody elicited by vaccination with the S2 cell expressed E2 in association with QS-21 would react with the Baculovirus expressed E2 protein, a preference for reaction with the S2 cell expressed ΔΔE2 is evident. No other antigen/adjuvant combination resulted in a specific anti-ΔΔE2 antibody response.

Based on the results of the lymphocyte stimulation experiment and the cytokine data, we expected the specific anti-antigen antibody level would be higher. In addition, we predicted that mice immunized with the antigen/antigen combination of ΔΔE2-MPL/TDM would have resulted in antibody production. The fact that this combination resulted in poor antibody production would not have been predicted from the lymphocyte stimulation data and the cytokine data. As has been discussed earlier, despite the fact that these adjuvants have been shown to work well with a variety of other immunogens, alum and MPL/TDM do not appropriately activate the immune response of mice. This demonstrates the empiric nature of establishing effectiveness of antigen/adjuvant formulation, that is effective formulations cannot be predicted based on the literature or isolated experiments, but must be determined in individually.

REFERENCES

Allander, T., A. Beyene, S. H. Jacobson, L. Grillner, and M. A. Persson. 1997. Patients infected with the same hepatitis C virus strain display different kinetics of the isolate-specific antibody response. J Infect Dis 175: 26–31.

Ausubel, F. A., R. Brent, R. E. Kingston, D. D. Moore, J. G. Seidman, J. A. Smith, and K. Struh. (eds.) 1999. Current Protocols in Molecular Biology. John Wiley & Sons. New York Bhandari, B. N., and T. L. Wright. 1995. Hepatitis C: an overview. Annu Rev Med 46: 309–17.

Chien, D. Y., Q. L. Choo, A. Tabrizi, C. Kuo, J. McFarland, K. Berger, C. Lee, J. R. Shuster, T. Nguyen, D. L. Moyer, and et al. 1992. Diagnosis of hepatitis C virus (HCV) infection using an immunodominant chimeric polyprotein to capture circulating antibodies: reevaluation of the role of HCV in liver disease. Proc Natl Acad Sci U S A 89: 10011–5.

Choo, Q. L., G. Kuo, R. Ralston, A. Weiner, D. Chien, G. Van Nest, J. Han, K. Berger, K. Thudium, C. Kuo, and et al. 1994. Vaccination of chimpanzees against infection by the hepatitis C virus. Proc Natl Acad Sci U S A 91: 1294–8.

Clarke, B. 1997. Molecular virology of hepatitis C virus. J Gen Virol 78 (Pt 10): 2397–410.

Cocquerel, L., J. C. Meunier, A. Pillez, C. Wychowski, and J. Dubuisson. 1998. A retention signal necessary and sufficient for endoplasmic reticulum localization maps to the transmembrane domain of hepatitis C virus glycoprotein E2. J Virol 72: 2183–91.

Culp, J. S., H. Johansen, B. Hellmig, J. Beck, T. J. Matthews, A. Delers, and M. Rosenberg. 1991. Regulated expression allows high level production and secretion of HIV-1 gp120 envelope glycoprotein in Drosophila Schneider cells. Biotechnology (N Y) 9: 173–7.

Deleersnyder, V., A. Pillez, C. Wychowski, K. Blight, J. Xu, Y. S. Hahn, C. M. Rice, and J. Dubuisson. 1997. Formation of native hepatitis C virus glycoprotein complexes. J Virol 71: 697–704.

Dubuisson, J., and C. M. Rice. 1996. Hepatitis C virus glycoprotein folding: disulfide bond formation and association with calnexin. J Virol 70: 778–86.

Dubuisson, J., H. H. Hsu, R. C. Cheung, H. B. Greenberg, D. G. Russell, and C. M. Rice. 1994. Formation and intracellular localization of hepatitis C virus envelope glycoprotein complexes expressed by recombinant vaccinia and Sindbis viruses. J Virol 68: 6147–60.

Esumi, M., T. Rikihisa, S. Nishimura, J. Goto, K. Mizuno, Y. H. Zhou, and T. Shikata. 1999. Experimental vaccine activities of recombinant E1 and E2 glycoproteins and hypervariable region 1 peptides of hepatitis C virus in chimpanzees. Arch Virol 144: 973–80.

Farci, P., A. Shimoda, D. Wong, T. Cabezon, D. De Gioannis, A. Strazzera, Y. Shimizu, M. Shapiro, H. J. Alter, and R. H. Purcell. 1996. Prevention of hepatitis C virus infection in chimpanzees by hyperimmune serum against the hypervariable region 1 of the envelope 2 protein. Proc Natl Acad Sci U S A 93: 15394–9.

Farci, P., H. J. Alter, S. Govindarajan, D. C. Wong, R. Engle, R. R. Lesniewski, I. K. Mushahwar, S. M. Desai, R. H. Miller, N. Ogata, and et al. 1992. Lack of protective immunity against reinfection with hepatitis C virus. Science 258: 135–40.

Flint, M., J. M. Thomas, C. M. Maidens, C. Shotton, S. Levy, W. S. Barclay, and J. A. McKeating. 1999a. Functional analysis of cell surface-expressed hepatitis C virus E2 glycoprotein. J Virol 73: 6782–90.

Flint, M., C. Maidens, L. D. Loomis-Price, C. Shotton, J. Dubuisson, P. Monk, A. Higginbottom, S. Levy, and J. A. McKeating. 1999b. Characterization of hepatitis C virus E2 glycoprotein interaction with a putative cellular receptor, CD81. J Virol 73: 6235–44.

Forns, X., T. Allander, P. Rohwer-Nutter, and J. Bukh. 2000a. Characterization of modified hepatitis C virus E2 proteins expressed on the cell surface. Virology 274: 75–85.

Forns, X., R. Thimme, S. Govindarajan, S. U. Emerson, R. H. Purcell, F. V. Chisari, and J. Bukh. 2000b. Hepatitis C virus lacking the hypervariable region 1 of the second envelope protein is infectious and causes acute resolving or persistent infection in chimpanzees. Proc Natl Acad Sci U S A 97: 13318–23.

Forns, X., P. J. Payette, X. Ma, W. Satterfield, G. Eder, I. K. Mushahwar, S. Govindarajan, H. L. Davis, S. U. Emerson, R. H. Purcell, and J. Bukh. 2000c. Vaccination of chimpanzees with plasmid DNA encoding the hepatitis C virus (HCV) envelope E2 protein modified the infection after challenge with homologous monoclonal HCV. Hepatology 32: 618–25.

Goto, J., S. Nishimura, M. Esumi, K. Makizumi, T. Rikihisa, T. Nishihara, K. Mizuno, Y. Zhou, T. Shikata, S. Fujiyama, and K. Tomita. 2001. Prevention of hepatitis C virus infection in a chimpanzee by vaccination and epitope mapping of antiserum directed against hypervariable region 1. Hepatol Res 19: 270–283.

Hadlock, K. G., R. E. Lanford, S. Perkins, J. Rowe, Q. Yang, S. Levy, P. Pileri, S. Abrignani, and S. K. Foung. 2000. Human monoclonal antibodies that inhibit binding of hepatitis C virus E2 protein to CD81 and recognize conserved conformational epitopes. J Virol 74: 10407–16.

Harada, S., R. Suzuki, A. Ando, Y. Watanabe, S. Yagi, T. Miyamura, and I. Saito. 1995. Establishment of a cell line constitutively expressing E2 glycoprotein of hepatitis C virus and humoral response of hepatitis C patients to the expressed protein. J Gen Virol 76: 1223–31.

Heile, J. M., Y. L. Fong, D. Rosa, K. Berger, G. Saletti, S. Campagnoli, G. Bensi, S. Capo, S. Coates, K. Crawford, C. Dong, M. Wininger, G. Baker, L. Cousens, D. Chien, P. Ng, P. Archangel, G. Grandi, M. Houghton, and S. Abrignani. 2000. Evaluation of hepatitis C virus glycoprotein E2 for vaccine design: an endoplasmic reticulum-retained recombinant protein is superior to secreted recombinant protein and DNA-based vaccine candidates. J Virol 74: 6885–92.

Hijikata, M., N. Kato, Y. Ootsuyama, M. Nakagawa, S. Ohkoshi, and K. Shimotohno. 1991. Hypervariable regions in the putative glycoprotein of hepatitis C virus. Biochem Biophys Res Commun 175: 220–8.

Hoofnagle, J. H. 1997. Hepatitis C: the clinical spectrum of disease. Hepatology 26: 15S-20S.

Inudoh, M., N. Kato, and Y. Tanaka. 1998. New monoclonal antibodies against a recombinant second envelope protein of Hepatitis C virus. Microbiol Immunol 42: 875–7.

Inudoh, M., H. Nyunoya, T. Tanaka, M. Hijikata, N. Kato, and K. Shimotohno. 1996. Antigenicity of hepatitis C virus envelope proteins expressed in Chinese hamster ovary cells. Vaccine 14: 1590–6.

Ishii, K., D. Rosa, Y. Watanabe, T. Katayama, H. Harada, C. Wyatt, K. Kiyosawa, H. Aizaki, Y. Matsuura, M. Houghton, S. Abrignani, and T. Miyamura. 1998. High titers of antibodies inhibiting the binding of envelope to human cells correlate with natural resolution of chronic hepatitis C. Hepatology 28: 1117–20.

Ivey-Hoyle, M., J. S. Culp, M. A. Chaikin, B. D. Hellmig, T. J. Matthews, R. W. Sweet, and M. Rosenberg. 1991. Envelope glycoproteins from biologically diverse isolates of immunodeficiency viruses have widely different affinities for CD4. Proc Natl Acad Sci U S A 88: 512–6.

Kato, N., H. Sekiya, Y. Ootsuyama, T. Nakazawa, M. Hijikata, S. Ohkoshi, and K. Shimotohno. 1993. Humoral immune response to hypervariable region 1 of the putative envelope glycoprotein (gp70) of hepatitis C virus. J Virol 67: 3923–30.

Kuroda, K., H. Geyer, R. Geyer, W. Doerfler, and H. D. Klenk. 1990. The oligosaccharides of influenza virus hemagglutinin expressed in insect cells by a baculovirus vector. Virology 174: 418–29.

Lai, M. E., A. P. Mazzoleni, F. Argiolu, S. De Virgilis, A. Balestrieri, R. H. Purcell, A. Cao, and P. Farci. 1994. Hepatitis C virus in multiple episodes of acute hepatitis in polytransfused thalassaemic children. Lancet 343: 388–90.

Lanford, R. E., L. Notvall, D. Chavez, R. White, G. Frenzel, C. Simonsen, and J. Kim. 1993. Analysis of hepatitis C virus capsid, E1, and E2/NS1 proteins expressed in insect cells. Virology 197: 225–35.

Lechner, S., K. Rispeter, H. Meisel, W. Kraas, G. Jung, M. Roggendorf, and A. Zibert. 1998. Antibodies directed to Envelope proteins of hepatitis c virus outside of hypervariable region 1. virology 243: 313–321.

Lee, K. J., Y. A. Suh, Y. G. Cho, Y. S. Cho, G. W. Ha, K. H. Chung, J. H. Hwang, Y. D. Yun, D. S. Lee, C. M. Kim, and Y. C. Sung. 1997. Hepatitis C virus E2 protein purified from mammalian cells is frequently recognized by E2-specific antibodies in patient sera. J Biol Chem 272: 30040–6.

Leon, P., J. A. Lopez, C. Elola, C. J. Domingo, and J. M. Echevarria. 1996. Detection of antibody to hepatitis C virus E2 recombinant antigen among samples indeterminate for anti-HCV after wide serological testing and correlation with viremia. The Spanish Study Group for Blood Donors at Risk of Transmission of HCV. Vox Sang 70: 213–6.

Lesniewski, R., G. Okasinski, R. Carrick, C. Van Sant, S. Desai, R. Johnson, J. Scheffel, B. Moore, and I. Mushahwar. 1995. Antibody to hepatitis C virus second envelope (HCV-E2) glycoprotein: a new marker of HCV infection closely associated with viremia. J Med Virol 45: 415–22.

Matsuura, Y., S. Harada, R. Suzuki, Y. Watanabe, Y. Inoue, I. Saito, and T. Miyamura. 1992. Expression of processed envelope protein of hepatitis C virus in mammalian and insect cells. J Virol 66: 1425–31.

Michalak, J. P., C. Wychowski, A. Choukhi, J. C. Meunier, S. Ung, C. M. Rice, and J. Dubuisson. 1997. Characterization of truncated forms of hepatitis C virus glycoproteins. J Gen Virol 78: 2299–306.

Mita, E., N. Hayashi, K. Ueda, A. Kasahara, H. Fusamoto, A. Takamizawa, K. Matsubara, H. Okayama, and T. Kamada. 1992. Expression of MBP-HCV NS1I/E2 fusion protein in E. coli and detection of anti-NS1/E2 antibody in type C chronic liver disease. Biochem Biophys Res Commun 183: 925–30.

Mondelli, M. U., A. Cerino, A. Lisa, S. Brambilla, L. Segagni, A. Cividini, M. Bissolati, G. Missale, G. Bellati, A. Meola, B. Bruniercole, A. Nicosia, G. Galfre, and E. Silini. 1999. Antibody responses to hepatitis C virus hypervariable region 1: evidence for cross-reactivity and immune-mediated sequence variation. Hepatology 30: 537–45.

Moore, J. P., J. A. McKeating, I. M. Jones, P. E. Stephens, G. Clements, S. Thomson, and R. A. Weiss. 1990. Characterization of recombinant gp120 and gp160 from HIV-1: binding to monoclonal antibodies and soluble CD4. Aids 4: 307–15.

Murphy, C. I., J. R. McIntire, D. R. Davis, H. Hodgdon, J. R. Seals, and E. Young. 1993. Enhanced expression, secretion, and large-scale purification of recombinant HIV-1 gp120 in insect cell using the baculovirus egt and p67 signal peptides. Protein Expr Purif 4: 349–57.

Nakamoto, Y., S. Kaneko, H. Ohno, M. Honda, M. Unoura, S. Murakami, and K. Kobayashi. 1996. B-cell epitopes in hypervariable region 1 of hepatitis C virus obtained from patients with chronic persistent hepatitis. J Med Virol 50: 35–41.

Nishihara, T., C. Nozaki, H. Nakatake, K. Hoshiko, M. Esumi, N. Hayashi, K. Hino, F. Hamada, K. Mizuno, and T. Shikata. 1993. Secretion and purification of hepatitis C virus NS 1 glycoprotein produced by recombinant baculovirus-infected insect cells. Gene 129: 207–14.

Ogata, N., H. J. Alter, R. H. Miller, and R. H. Purcell. 1991. Nucleotide sequence and mutation rate of the H strain of hepatitis C virus. Proc Natl Acad Sci U S A 88: 3392–6.

Pileri, P., Y. Uematsu, S. Campagnoli, G. Galli, F. Falugi, R. Petracca, A. J. Weiner, M. Houghton, D. Rosa, G. Grandi, and S. Abrignani. 1998. Binding of hepatitis C virus to CD81. Science 282: 938–41.

Proust, B., F. Dubois, Y. Bacq, S. Le Pogam, S. Rogez, R. Levillain, and A. Goudeau. 2000. Two Successive Hepatitis C Virus Infections in an Intravenous Drug User. J Clin Microbiol 38: 3125–3127.

Psichogiou, M., A. Katsoulidou, E. Vaindirli, B. Francis, S. R. Lee, and A. Hatzakis. 1997. Immunologic events during the incubation period of hepatitis C virus infection: the role of antibodies to E2 glycoprotein. Multicentre Hemodialysis Cohort Study on Viral Hepatitis. Transfusion 37: 858–62.

Purcell, R. 1997. The hepatitis C virus: overview. Hepatology 26: 11S-14S.

Ralston, R., K. Thudium, K. Berger, C. Kuo, B. Gervase, J. Hall, M. Selby, G. Kuo, M. Houghton, and Q. L. Choo. 1993. Characterization of hepatitis C virus envelope glycoprotein complexes expressed by recombinant vaccinia viruses. J Virol 67: 6753–61.

Ray, S. C., Y. M. Wang, O. Laeyendecker, J. R. Ticehurst, S. A. Villano, and D. L. Thomas. 1999. Acute hepatitis C virus structural gene sequences as predictors of persistent viremia: hypervariable region 1 as a decoy. J Virol 73: 2938–46.

Robertson, B., G. Myers, C. Howard, T. Brettin, J. Bukh, B. Gaschen, T. Gojobori, G. Maertens, M. Mizokami, O. Nainan, S. Netesov, K. Nishioka, T. Shin i, P. Simmonds, D. Smith, L. Stuyver, and A. Weiner. 1998. Classification, nomenclature, and database development for hepatitis C virus (HCV) and related viruses: proposals for standardization. International Committee on Virus Taxonomy. Arch Virol 143: 2493–503.

Rosa, D., S. Campagnoli, C. Moretto, E. Guenzi, L. Cousens, M. Chin, C. Dong, A. J. Weiner, J. Y. Lau, Q. L. Choo, D. Chien, P. Pileri, M. Houghton, and S. Abrignani. 1996. A quantitative test to estimate neutralizing antibodies to the hepatitis C virus: cytofluorimetric assessment of envelope glycoprotein 2 binding to target cells. Proc Natl Acad Sci U S A 93: 1759–63.

Sambrook, J., E. R. Fritsch, T. Maniatis. 1989. Molecular Cloning, A Laboratory Manuel, Second Edition. Cold Spring Harbor Laboratory, Cold Spring Harbor, N.Y.

Spaete, R. R., D. Alexander, M. E. Rugroden, Q. L. Choo, K. Berger, K. Crawford, C. Kuo, S. Leng, C. Lee, R. Ralston, and et al. 1992. Characterization of the hepatitis C virus E2/NS1 gene product expressed in mammalian cells. Virology 188: 819–30.

van der Staten, A., H. Johnsen, M. Rosenbert, and R. W. Sweet. 1989. Introduction and constitutive expression of gene products in cultured Drosophila cell using hygromycin B. selection. M. Mol. Cell Bio. 1:1–8.

van Doorn, L. J., I. Capriles, G. Maertens, R. DeLeys, K. Murray, T. Kos, H. Schellekens, and W. Quint. 1995. Sequence evolution of the hypervariable region in the putative envelope region E2/NS 1 of hepatitis C virus is correlated with specific humoral immune responses. J Virol 69: 773–8.

Weiner, A. J., M. J. Brauer, J. Rosenblatt, K. H. Richman, J. Tung, K. Crawford, F. Bonino, G. Saracco, Q. L. Choo, M. Houghton, and et al. 1991. Variable and hypervariable domains are found in the regions of HCV corresponding to the flavivirus envelope and NS1 proteins and the pestivirus envelope glycoproteins. Virology 180: 842–8.

Wigler, M., A. Pellicer, S. Silverstein, R. Axel, G. Urlaub, and L. Chasin. 1979. DNA-mediated transfer of the adenine phosphoribosyltransferase locus into mammalian cells. Proc Natl Acad Sci U S A 76: 1373–6.

Wyatt, C. A., L. Andrus, B. Brotman, F. Huang, D. H. Lee, and A. M. Prince. 1998. Immunity in chimpanzees chronically infected with hepatitis C virus: role of minor quasispecies in reinfection. J Virol 72: 1725–30.

Yanagi, M., R. H. Purcell, S. U. Emerson, and J. Bukh. 1997. Transcripts from a single full-length cDNA clone of hepatitis C virus are infectious when directly transfected into the liver of a chimpanzee. Proc Natl Acad Sci U S A 94: 8738–43.

Yanagi, M., M. St Claire, M. Shapiro, S. U. Emerson, R. H. Purcell, and J. Bukh. 1998. Transcripts of a chimeric cDNA clone of hepatitis C virus genotype 1b are infectious in vivo. Virology 244: 161–72.

Yuki, N., N. Hayashi, A. Kasahara, H. Hagiwara, E. Mita, K. Ohkawa, K. Katayama, H. Fusamoto, and T. Kamada. 1996. Quantitative analysis of antibody to hepatitis C virus envelope 2 glycoprotein in patients with chronic hepatitis C virus infection. Hepatology 23: 947–52.

Zibert, A., H. Meisel, W. Kraas, A. Schulz, G. Jung, and M. Roggendorf. 1997. Early antibody response against hypervariable region 1 is associated with acute self-limiting infections of hepatitis C virus. Hepatology 25: 1245–9.

Zibert, A., W. Kraas, R. S. Ross, H. Meisel, S. Lechner, G. Jung, and M. Roggendorf. 1999. Immunodominant B-cell domains of hepatitis C virus envelope proteins E1 and E2 identified during early and late time points of infection. J Hepatol 30: 177–84.

Although the invention has been described with reference to the presently preferred embodiment, it should be understood that various modifications can be made without departing from the spirit of the invention. Accordingly, the invention is limited only by the following claims.

What is claimed is:

1. A secreted polypeptide comprising: a hepatitis C virus (HCV) E2 Polypeptide, lacking all or a portion of its membrane spanning domain such that said E2 polypeptide is capable of secretion into growth medium when expressed recombinantly in host cell, and further comprising a deletion in at least a portion of its N-terminus ending at about amino acid residue 411, numbered with reference to the HCV E2 amino acid sequence (SEQ ID NO:9).

2. A secreted polypeptide comprising: a hepatitis C virus (HCV) E2 polypeptide, lacking all or a portion of its membrane spanning domain such that said E2 polypeptide is capable of secretion into growth medium when expressed recombinantly in a host cell, wherein said E2 polypeptide lacks at least a portion of its C-terminus beginning at about amino acid residue 662 and at least a portion of its N-terminus ending at about amino acid residue 411, numbered with reference to the HCV E2 amino acid sequence (SEQ ID NO:9).

3. A purified immunogenic polypeptide comprising the polypeptide of claim 1.

4. The immunogenic polypeptide of claim 3, wherein the amino acid sequence is set forth in SEQ ID NO.8.

5. The immunogenic polypeptide of claim 3, wherein the host cells are insect cells.

6. The immunogenic polypeptide of claim 5, wherein the insect cells are Drosophila cells.

7. The immunogenic polypeptide of claim 6, wherein the insect cells are S2 cells.

8. The immunogenic polypeptide of claim 1, wherein the immunogenic polypeptide is a monomer.

9. The immunogenic polypeptide of claim 1, wherein the immunogenic polypeptide is glycosylated.

10. A composition comprising an immunogenic polypeptide of claim 1 and a pharmaceutically acceptable carrier.

11. A composition comprising an immunogenic polypeptide of claim 1 and an adjuvant.

12. The composition of claim 11, wherein the adjuvant is QS-21.

13. A kit useful for providing immune protection for HCV comprising a container containing a polypeptide of claim 1 and a pharmaceutically acceptable carrier.

14. A immunoprotective composition comprising the polypeptide of claim 3.

15. The composition of claim 14, further comprising an immunomodulatory agent.

16. The composition of claim 15, wherein the immunomodulatory agent is IL-2, GM-CSF, IL-12, gamma-interferon, IP-10, MIP1.beta., or RANTES.

17. A method of treating HCV infection comprising administering to a subject having or at risk of having HCV infection an effective amount of the immunogenic polypeptide of claim 3, thereby treating the infection.

18. The method of claim 17, further comprising administering an immunomodulatory agent.

19. The method of claim 18, wherein the immunomodulatory agent is IL-2, GM-CSF, IL-12, gamma-interferon, IP-10, MIP 1.beta., or RANTES.

20. A method of providing immune protection against HCV comprising administering to a subject in need of protection an effective amount of the immunogenic polypeptide of claim 3, thereby providing protection from HCV infection.

21. The method of claim 20 further comprising administering an immunomodulatory agent.

22. The method of claim 21, wherein the immunomodulatory agent is IL-2, GM-CSF, IL-12, gamma-interferon, IP-10, MIP1.beta., or RANTES.

23. A method of preparing an HCV E2 immunogenic polypeptide of claim 1 comprising expressing a polynucleotide sequence encoding the HCV E2 immunogenic polypeptide in an insect cell line and culturing the cells under conditions which provide HCV E2 polypeptide of claim 1.

24. The method of claim 23, wherein the insect cell line is Drosophila S2 cell line.

25. The method of claim 24, wherein the HCV E2 polypeptide is lacking all or a portion of its membrane spanning domain such that said E2 polypeptide is capable of secretion into growth medium when expressed recombinantly in a host cell, wherein said E2 polypeptide lacks at least a portion of its C-terminus beginning at about amino acid residue 662 and at least a portion of its N terminus ending at about amino acid residue 411, numbered with reference to the HCV E2 amino acid sequence (SEQ ID NO:9).

26. A method for preparing an immunogenic composition for treatment of HCV comprising: (a) forming an immunogenic polypeptide composition comprising a polypeptide of claim 1, wherein the immunogenic polypeptide composition is suitable for treating HCV; (b) providing a suitable excipient; and (c) mixing the immunogenic composition of (a) with the excipient of (b).

27. A method of producing anti-HCV antibodies comprising administering to a mammal an effective amount of an immunogenic polypeptide composition comprising a hepatitis C virus (HCV) E2 polypeptide, lacking all or a portion of its membrane spanning domain such that said E2 polypeptide is capable of secretion into growth medium when expressed recombinantly in a host cell, and further comprising a deletion in at least a portion of its N-terminus ending at about amino acid residue 411, numbered with reference to the HCV E2 amino acid sequence (SEQ ID NO:9).

28. A polyclonal antibody composition made according to the method of claim 27.

29. A purified antibody that specifically binds to a polypeptide of claim 1.

30. A secreted polypeptide comprising: a hepatitis C virus (HCV) E2 polypeptide, lacking all or a portion of its membrane spanning domain such that said E2 polypeptide is capable of secretion into growth medium when expressed recombinantly in a host cell, wherein said E2 polypeptide lacks at least a portion of its C-terminus beginning at about amino acid residue 662 and at least a portion of its N-terminus ending at about amino acid residue 411, numbered with reference to the HCV E2 amino acid sequence (SEQ ID NO:9), wherein said polypeptide is produced recombinantly in insect host cells.

31. The polypeptide of claim 30, wherein the insect cells are Drosophila cells.

32. An isolated polynucleotide encoding a polypeptide of claim 1.

33. The polynucleotide of claim 32, wherein the polynucleotide is set forth in SEQ ID NO:1.

34. The polynucleotide of claim 32, wherein the polypeptide has an amino acid sequence as set forth in SEQ ID NO:8.

35. A method of detecting the presence of HCV in a sample comprising contacting the sample with an antibody of claim 29 and detecting binding of the antibody to the polypeptide, wherein formation of a complex between the antibody and the E2 polypeptide is indicative of the presence of HCV in the sample.

36. The method of claim 35, wherein the antibody is detectably labeled.

37. A method of detecting HCV infection comprising contacting a biological sample with the immunogenic polypeptide of claim 3 under conditions which allow formation of an antibody-antigen complex and detecting said complex.

38. The method of claim 37, wherein the antigen is detectably labeled.

39. A polypeptide capable of secretion into growth medium when expressed recombinantly in a host cell, comprising:
a hepatitis C virus (HCV) E2 polypeptide lacking all or a portion of its membrane spanning domain and lacking at least a portion of its HVR-1 domain, wherein the polypeptide is recognized by conformationally sensitive monoclonal antibodies.

40. A polypeptide capable of secretion into growth medium when expressed recombinantly in a host cell, comprising:
a hepatitis C virus (HCV) E2 polypeptide lacking all or a portion of its membrane spanning domain and further lacking most or all of its HVR-1 domain, wherein the polypeptide is recognized by conformationally sensitive monoclonal antibodies.

41. A purified immunogenic polypeptide comprising the polypeptide of claim 39 or 40.

42. The immunogenic polypeptide of claim 41, wherein the host cells are insect cells.

43. The immunogenic polypeptide of claim 42, wherein the insect cells are Drosophila cells.

44. The immunogenic polypeptide of claim 43, wherein the Drosophila cells are S2 cells.

45. The immunogenic polypeptide of claim 39 or 40, wherein the immunogenic polypeptide is a monomer.

46. The immunogenic polypeptide of claim 39 or 40, wherein the immunogenic polypeptide is glycosylated.

47. A composition comprising an immunogenic polypeptide of claim 39 or 40, and a pharmaceutically acceptable carrier.

48. A composition comprising an immunogenic polypeptide of claim 39 or 40, and an adjuvant.

49. The composition of claim 48, wherein the adjuvant is QS-21.

50. A kit useful for providing immune protection for HCV comprising a container containing a polypeptide of claim 39 or 40, and a pharmaceutically acceptable carrier.

51. A immunoprotective composition comprising the polypeptide of claim 41.

52. The composition of claim 51, further comprising an immunomodulatory agent.

53. The composition of claim 52, wherein the immunomodulatory agent is IL-2, GM-CSF, IL-12, gamma-interferon, IP-10, MIP1β, or RANTES.

54. A method of treating HCV infection comprising administering to a subject having or at risk of having HCV infection an effective amount of the immunogenic polypeptide of claim 41, thereby treating the infection.

55. The method of claim 54, further comprising administering an immunomodulatory agent.

56. The method of claim 55, wherein the immunomodulatory agent is IL-2, GM-CSF, IL-12, gamma-interferon, IP-10, MIP1β, or RANTES.

57. A method of providing immune protection against HCV comprising administering to a subject in need of protection an effective amount of the immunogenic polypeptide of claim 41, thereby providing protection from HCV infection.

58. The method of claim 57 further comprising administering an immunomodulatory agent.

59. The method of claim 58, wherein the immunomodulatory agent is IL-2, GM-CSF, IL-12, gamma-interferon, IP-10, MIP1β, or RANTES.

60. A method of preparing an HCV E2 immunogenic polypeptide of claim 39 or 40 comprising expressing a polynucleotide sequence encoding the HCV E2 immunogenic polypeptide in an insect cell line and culturing the cells under conditions which provide HCV E2 polypeptide of claim 39 or 40, respectively.

61. The method of claim 60, wherein the insect cell line is Drosophila S2 cell line.

62. A method for preparing an immunogenic composition for treatment of HCV comprising:

(a) forming an immunogenic polypeptide composition comprising a polypeptide of claim 39 or 40, wherein the immunogenic polypeptide composition is suitable for treating HCV;

(b) providing a suitable excipient; and (c) mixing the immunogenic composition of (a) with the excipient of (b).

63. A method of producing anti-HCV antibodies comprising administering to a mammal an effective amount of an immunogenic polypeptide composition comprising a hepatitis C virus (HCV) E2 polypeptide, lacking all or a portion of its membrane spanning domain such that said E2 polypeptide is capable of secretion into growth medium when expressed recombinantly in a host cell, and further lacking its HVR-1 domain, and wherein the polypeptide is recognized by conformationally sensitive monoclonal antibodies.

64. A polyclonal antibody composition made according to the method of claim 63.

65. A purified antibody that specifically binds to a polypeptide of claim 39 or 40.

66. A polypeptide capable of secretion into growth medium when expressed recombinantly in an insect host cell, comprising:

a hepatitis C virus (HCV) E2 polypeptide lacking all or a portion of its membrane spanning domain and lacking all or a portion of its HVR-1 domain, wherein the polypeptide is recognized by conformationally sensitive monoclonal antibodies.

67. The polypeptide of claim 66, wherein the insect cells are Drosophila cells.

68. An isolated polynucleotide encoding a polypeptide of claim 39 or 40.

69. A method of detecting the presence of HCV in a sample comprising contacting the sample with an antibody of claim 65 and detecting binding of the antibody to the polypeptide, wherein formation of a complex between the antibody and the E2 polypeptide is indicative of the presence of HCV in the sample.

70. The method of claim 69, wherein the antibody is detectably labeled.

71. A method of detecting HCV infection comprising contacting a biological sample with the immunogenic polypeptide of claim 41 under conditions which allow formation of an antibody-antigen complex and detecting said complex.

72. The method of claim 71, wherein the antigen is detectably labeled.

73. A polypeptide capable of secretion into growth medium when expressed recombinantly in a host cell, comprising:

a hepatitis C virus (HCV) E2 polypeptide lacking all or a portion of its membrane spanning domain and lacking at least a portion of its N-terminus ending at about amino acid residue 411, numbered with reference to the HCV E2 amino acid sequence (SEQ ID NO:9 as to polypeptide's N-terminus deletion), wherein the polypeptide is recognized by conformationally sensitive monoclonal antibodies.

74. A polypeptide capable of secretion into growth medium when expressed recombinantly in a host cell, comprising:

a hepatitis C virus (HCV) E2 polypeptide, lacking all or a portion of its membrane spanning domain and lacking all of its N-terminus ending at amino acid residue 411, numbered with reference to the HCV E2 amino acid sequence (SEQ ID NO:9 as to the polypeptide's N-terminus deletion), wherein the polypeptide is recognized by conformationally sensitive monoclonal antibodies.

75. A purified immunogenic polypeptide comprising the polypeptide of claim 73 or 74.

76. The immunogenic polypeptide of claim 75, wherein the amino acid sequence is set forth in SEQ ID NO:8 (using a C-terminus deletion point of 662 for illustration and not for limitation).

77. The immunogenic polypeptide of claim 75, wherein the host cells are insect cells.

78. The immunogenic polypeptide of claim 77, wherein the insect cells are Drosophila cells.

79. The immunogenic polypeptide of claim 78, wherein the Drosophila cells are S2 cells.

80. The immunogenic polypeptide of claim 73 or 74, wherein the immunogenic polypeptide is a monomer.

81. The immunogenic polypeptide of claim 73 or 74, wherein the immunogenic polypeptide is glycosylated.

82. A composition comprising an immunogenic polypeptide of claim 73 or 74, and a pharmaceutically acceptable carrier.

83. A composition comprising an immunogenic polypeptide of claim 73 or 74, and an adjuvant.

84. The composition of claim 83, wherein the adjuvant is QS-21.

85. A kit useful for providing immune protection for HCV comprising a container containing a polypeptide of claim 73 or 74, and a pharmaceutically acceptable carrier.

86. A immunoprotective composition comprising the polypeptide of claim 75.

87. The composition of claim 86, further comprising an immunomodulatory agent.

88. The composition of claim 87, wherein the immunomodulatory agent is IL-2, GM-CSF, IL-12, gamma-interferon, IP-10, MIP1β, or RANTES.

89. A method of treating HCV infection comprising administering to a subject having or at risk of having HCV infection an effective amount of the immunogenic polypeptide of claim 75, thereby treating the infection.

90. The method of claim 89, further comprising administering an immunomodulatory agent.

91. The method of claim 89, wherein the immunomodulatory agent is IL-2, GM-CSF, IL-12, gamma-interferon, IP-10, MIP1β, or RANTES.

92. A method of providing immune protection against HCV comprising administering to a subject in need of protection an effective amount of the immunogenic polypeptide of claim 75, thereby providing protection from HCV infection.

93. The method of claim 92 further comprising administering an immunomodulatory agent.

94. The method of claim 93, wherein the immunomodulatory agent is IL-2, GM-CSF, IL-12, gamma-interferon, IP-10, MIP1β, or RANTES.

95. A method of preparing an HCV E2 immunogenic polypeptide of claim 73 or 74, comprising expressing a polynucleotide sequence encoding the HCV E2 immunogenic polypeptide in an insect cell line and culturing the cells under conditions which provide HCV E2 polypeptide of claim 39 or 40, respectively.

96. The method of claim 95, wherein the insect cell line is Drosophila S2 cell line.

97. The method of claim 96, wherein the HCV E2 polypeptide is lacking all or a portion of its membrane spanning domain such that said E2 polypeptide is capable of secretion into growth medium when expressed recombinantly in a host cell, wherein said E2 polypeptide lacks at least a portion of its N-terminus ending at about amino acid residue 411, numbered with reference to the HCV E2 amino acid sequence (SEQ ID NO:9 as to the polypeptide's N-terminus deletion).

98. A method for preparing an immunogenic composition for treatment of HCV comprising:
(a) forming an immunogenic polypeptide composition comprising a polypeptide of claim 73 or 74, wherein the immunogenic polypeptide composition is suitable for treating HCV;
(b) providing a suitable excipient; and
(c) mixing the immunogenic composition of (a) with the excipient of (b).

99. A method of producing anti-HCV antibodies comprising administering to a mammal an effective amount of an immunogenic polypeptide composition comprising a hepatitis C virus (HCV) E2 polypeptide, lacking all or a portion of its membrane spanning domain such that said E2 polypeptide is capable of secretion into growth medium when expressed recombinantly in a host cell, and further comprising a deletion in at least a portion of its N-terminus ending at about amino acid residue 411, numbered with reference to the HCV E2 amino acid sequence (SEQ ID NO:9 as to the polypeptide's N-terminus deletion), wherein the polypeptide is recognized by conformationally sensitive monoclonal antibodies.

100. A polyclonal antibody composition made according to the method of claim 99.

101. A purified antibody that specifically binds to a polypeptide of claim 73 or 74.

102. A polypeptide capable of secretion into growth medium when expressed recombinantly in an insect host cell, comprising:
a hepatitis C virus (HCV) E2 polypeptide lacking all or a portion of its membrane spanning domain and lacking at least a portion of its N-terminus ending at about amino acid residue 411, numbered with reference to the HCV E2 amino acid sequence (SEQ ID NO:9 at to the polypeptide's N-terminus deletion), wherein the polypeptide is recognized by conformationally sensitive monoclonal antibodies.

103. The polypeptide of claim 102, wherein the insect cells are Drosophila cells.

104. An isolated polynucleotide encoding a polypeptide of claim 73 or 74.

105. The polynucleotide of claim 104, wherein the polynucleotide is set forth in SEQ ID NO: 1 as to the polypeptide's N-terminus deletion.

106. The polynucleotide of claim 104, wherein the polypeptide has an amino acid sequence as set forth in SEQ ID NO:8 as to the polypeptide's N-terminus deletion.

107. A method of detecting the presence of HCV in a sample comprising contacting the sample with an antibody of claim 101 and detecting binding of the antibody to the polypeptide, wherein formation of a complex between the antibody and the E2 polypeptide is indicative of the presence of HCV in the sample.

108. The method of claim 107, wherein the antibody is detectably labeled.

109. A method of detecting HCV infection comprising contacting a biological sample with the immunogenic polypeptide of claim 75 under conditions which allow formation of an antibody-antigen complex and detecting said complex.

110. The method of claim 109, wherein the antigen is detectably labeled.

111. A polypeptide capable of secretion into growth medium when expressed recombinantly in a host cell, comprising:
a hepatitis C virus (HCV) E2 polypeptide lacking all or a portion of its C-terminus beginning at about amino acid residue 662 and further lacking all or a portion of its N-terminus ending at about amino acid residue 411, numbered with reference to the HCV E2 amino acid sequence (SEQ ID NO:9).

112. A polypeptide capable of secretion into growth medium when expressed recombinantly in a host cell, comprising:
a hepatitis C virus (HCV) E2 polypeptide lacking all or a portion of its C-terminus beginning at amino acid residue 662 and further lacking all or a portion of its N-terminus ending at amino acid residue 411, numbered with reference to the HCV E2 amino acid sequence (SEQ ID NO:9).

113. A purified immunogenic polypeptide comprising the polypeptide of claim 111 or 112.

114. The immunogenic polypeptide of claim 113, wherein the amino acid sequence is set forth in SEQ ID NO:8.

115. The immunogenic polypeptide of claim 113, wherein the host cells are insect cells.

116. The immunogenic polypeptide of claim 115, wherein the insect cells are Drosophila cells.

117. The immunogenic polypeptide of claim 116, wherein the Drosophila cells are S2 cells.

118. The immunogenic polypeptide of claim 111 or 112, wherein the immunogenic polypeptide is a monomer.

119. The immunogenic polypeptide of claim 111 or 112, wherein the immunogenic polypeptide is glycosylated.

120. A composition comprising an immunogenic polypeptide of claim 111 or 112, and a pharmaceutically acceptable carrier.

121. A composition comprising an immunogenic polypeptide of claim 111 or 112, and an adjuvant.

122. The composition of claim 121, wherein the adjuvant is QS-21.

123. A kit useful for providing immune protection for HCV comprising a container containing a polypeptide of claim 111 or 112, and a pharmaceutically acceptable carrier.

124. A immunoprotective composition comprising the polypeptide of claim 113.

125. The composition of claim 124, further comprising an immunomodulatory agent.

126. The composition of claim 125, wherein the immunomodulatory agent is IL-2, GM-CSF, IL-12, gamma-interferon, IP-10, MIP1β, or RANTES.

127. A method of treating HCV infection comprising administering to a subject having or at risk of having HCV infection an effective amount of the immunogenic polypeptide of claim 113, thereby treating the infection.

128. The method of claim 127, further comprising administering an immunomodulatory agent.

129. The method of claim 128, wherein the immunomodulatory agent is IL-2, GM-CSF, IL-12, gamma-interferon, IP-10, MIP1β, or RANTES.

130. A method of providing immune protection against HCV comprising administering to a subject in need of protection an effective amount of the immunogenic polypeptide of claim 113, thereby providing protection from HCV infection.

131. The method of claim 130 further comprising administering an immunomodulatory agent.

132. The method of claim 131, wherein the immunomodulatory agent is IL-2, GM-CSF, IL-12, gamma-interferon, IP-10, MIP1β, or RANTES.

133. A method of preparing an HCV E2 immunogenic polypeptide of claim 111 or 112 comprising expressing a polynucleotide sequence encoding the HCV E2 immunogenic polypeptide in an insect cell line and culturing the cells under conditions which provide HCV E2 polypeptide of claim 111 or 112, respectively.

134. The method of claim 133, wherein the insect cell line is Drosophila S2 cell line.

135. The method of claim 134, wherein the HCV E2 polypeptide is capable of secretion into growth medium when expressed recombinantly in a host cell, wherein said E2 polypeptide lacks at least a portion of its C-terminus beginning at about amino acid residue 662 and at least a portion of its N-terminus ending at about amino acid residue 411, numbered with reference to the HCV E2 amino acid sequence (SEQ ID NO:9).

136. A method for preparing an immunogenic composition for treatment of HCV comprising:
(a) forming an immunogenic polypeptide composition comprising a polypeptide of claim 111 or 112, wherein the immunogenic polypeptide composition is suitable for treating HCV;
(b) providing a suitable excipient; and
(c) mixing the immunogenic composition of (a) with the excipient of (b).

137. A method of producing anti-HCV antibodies comprising administering to a mammal an effective amount of an immunogenic polypeptide composition comprising a hepatitis C virus (HCV) E2 polypeptide that is capable of secretion into growth medium when expressed recombinantly in a host cell, and further comprising a first deletion in at least a portion of its N-terminus ending at about amino acid residue 411 and a second deletion in at least a portion of its C-terminus ending at about amino acid residue 662, numbered with reference to the HCV E2 amino acid sequence (SEQ ID NO:9).

138. A polyclonal antibody composition made according to the method of claim 137.

139. A purified antibody that specifically binds to a polypeptide of claim 111 or 112.

140. A polypeptide comprising:
a hepatitis C virus (HCV) E2 polypeptide capable of secretion into growth medium when expressed recombinantly in a host cell, wherein said E2 polypeptide lacks at least a portion of its C-terminus beginning at about amino acid residue 662 and at least a portion of its N-terminus ending at about amino acid residue 411, numbered with reference to the HCV E2 amino acid sequence (SEQ ID NO:9), wherein said polypeptide is produced recombinantly in insect host cells.

141. The polypeptide of claim 140, wherein the insect cells are Drosophila cells.

142. An isolated polynucleotide encoding a polypeptide of claim 111 or 112.

143. The polynucleotide of claim 142, wherein the polynucleotide is set forth in SEQ ID NO:1.

144. The polynucleotide of claim 142, wherein the polypeptide has an amino acid sequence as set forth in SEQ ID NO:8.

145. A method of detecting the presence of HCV in a sample comprising contacting the sample with an antibody of claim 139 and detecting binding of the antibody to the polypeptide, wherein formation of a complex between the antibody and the E2 polypeptide is indicative of the presence of HCV in the sample.

146. The method of claim 145, wherein the antibody is detectably labeled.

147. A method of detecting HCV infection comprising contacting a biological sample with the immunogenic polypeptide of claim 113 under conditions which allow formation of an antibody-antigen complex and detecting said complex.

148. The method of claim 147, wherein the antigen is detectably labeled.

* * * * *

SEQUENCE LISTING

<160> NUMBER OF SEQ ID NOS: 9

<210> SEQ ID NO 1
<211> LENGTH: 750
<212> TYPE: DNA
<213> ORGANISM: Hepatitis C Virus

<400> SEQUENCE: 1

```
caactgatca acaccaacgg cagttggcac atcaatagca cggccttgaa ttgcaatgaa      60
agccttaaca ccggctggtt agcagggctc ttctatcaac acaaattcaa ctcttcaggc     120
tgtcctgaga ggttggccag ctgccgacgc cttaccgatt ttgcccaggg ctggggtcct     180
atcagttatg ccaacggaag cggcctcgac gaacgcccct actgctggca ctaccctcca     240
agaccttgtg gcattgtgcc cgcaaagagc gtgtgtggcc cggtatattg cttcactccc     300
agccccgtgg tggtgggaac gaccgacagg tcgggcgcgc ctacctacag ctggggtgca     360
aatgatacgg atgtcttcgt ccttaacaac accaggccac cgctgggcaa ttggttcggt     420
tgtacctgga tgaactcaac tggattcacc aaagtgtgcg gagcgccccc ttgtgtcatc     480 ggagggggtgg gcaacaacac cttgctctgc cccactgatt gcttccgcaa acatccggaa     540
```

```
gccacatact ctcggtgcgg ctccggtccc tggattacac ccaggtgcat ggtcgactac      600
ccgtataggc tttggcacta tccttgtacc atcaattaca ccatattcaa agtcaggatg      660
tacgtgggag gggtcgagca caggctggaa gcggcctgca actggacgcg gggcgaacgc      720
tgtgatctgg aagacaggga caggtccgag                                      750
```

```
<210> SEQ ID NO 2
<211> LENGTH: 33
<212> TYPE: DNA
<213> ORGANISM: Artificial sequence
<220> FEATURE:
<223> OTHER INFORMATION: Primer for PCR

<400> SEQUENCE: 2
caagatagat ctcaactgat caacaccaac ggc                                   33

<210> SEQ ID NO 3
<211> LENGTH: 39
<212> TYPE: DNA
<213> ORGANISM: Artificial sequence
<220> FEATURE:
<223> OTHER INFORMATION: Primer for PCR

<400> SEQUENCE: 3
ctactttcta gattactact cggacctgtc cctgtcttc                             39

<210> SEQ ID NO 4
<211> LENGTH: 33
<212> TYPE: DNA
<213> ORGANISM: Artificial sequence
<220> FEATURE:
<223> OTHER INFORMATION: Primer for PCR

<400> SEQUENCE: 4
caagatagat ctcagcttgt gaataccaac ggc                                   33

<210> SEQ ID NO 5
<211> LENGTH: 39
<212> TYPE: DNA
<213> ORGANISM: Artificial sequence
<220> FEATURE:
<223> OTHER INFORMATION: Primer for PCR

<400> SEQUENCE: 5
ctactttcta gattactatt ctgacctatc cctgtcctc                             39

<210> SEQ ID NO 6
<211> LENGTH: 37
<212> TYPE: DNA
<213> ORGANISM: Artificial sequence
<220> FEATURE:
<223> OTHER INFORMATION: Primer for PCR

<400> SEQUENCE: 6
attgaaagat ctgaaaccca cgtcaccggg ggaaatg                               37

<210> SEQ ID NO 7
<211> LENGTH: 32
<212> TYPE: DNA
<213> ORGANISM: Artificial sequence
<220> FEATURE:
<223> OTHER INFORMATION: Primer for PCR
```

<400> SEQUENCE: 7
gttgaaagat ctgagaccca cacgacgggg ag                                32

<210> SEQ ID NO 8
<211> LENGTH: 250
<212> TYPE: PRT
<213> ORGANISM: Hepatitis C Virus

<400> SEQUENCE: 8

Gln Leu Ile Asn Thr Asn Gly Ser Trp His Ile Asn Ser Thr Ala Leu
1               5                   10                  15

Asn Cys Asn Glu Ser Leu Asn Thr Gly Trp Leu Ala Gly Leu Phe Tyr
            20                  25                  30

Gln His Lys Phe Asn Ser Ser Gly Cys Pro Glu Arg Leu Ala Ser Cys
        35                  40                  45

Arg Arg Leu Thr Asp Phe Ala Gln Gly Trp Gly Pro Ile Ser Tyr Ala
    50                  55                  60

Asn Gly Ser Gly Leu Asp Glu Arg Pro Tyr Cys Trp His Tyr Pro Pro
65                  70                  75                  80

Arg Pro Cys Gly Ile Val Pro Ala Lys Ser Val Cys Gly Pro Val Tyr
                85                  90                  95

Cys Phe Thr Pro Ser Pro Val Val Gly Thr Thr Asp Arg Ser Gly
            100                 105                 110

Ala Pro Thr Tyr Ser Trp Gly Ala Asn Asp Thr Asp Val Phe Val Leu
        115                 120                 125

Asn Asn Thr Arg Pro Pro Leu Gly Asn Trp Phe Gly Cys Thr Trp Met
    130                 135                 140

Asn Ser Thr Gly Phe Thr Lys Val Cys Gly Ala Pro Pro Cys Val Ile
145                 150                 155                 160

Gly Gly Val Gly Asn Asn Thr Leu Leu Cys Pro Thr Asp Cys Phe Arg
                165                 170                 175

Lys His Pro Glu Ala Thr Tyr Ser Arg Cys Gly Ser Gly Pro Trp Ile
            180                 185                 190

Thr Pro Arg Cys Met Val Asp Tyr Pro Tyr Arg Leu Trp His Tyr Pro
        195                 200                 205

Cys Thr Ile Asn Tyr Thr Ile Phe Lys Val Arg Met Tyr Val Gly Gly
    210                 215                 220

Val Glu His Arg Leu Glu Ala Ala Cys Asn Trp Thr Arg Gly Glu Arg
225                 230                 235                 240

Cys Asp Leu Glu Asp Arg Asp Arg Ser Glu
                245                 250

<210> SEQ ID NO 9
<211> LENGTH: 3011
<212> TYPE: PRT
<213> ORGANISM: Hepatitic C Virus

<400> SEQUENCE: 9

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

-continued

```
Ile Pro Lys Ala Arg Arg Pro Glu Gly Arg Thr Trp Ala Gln Pro Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
        195                 200                 205

Asn Ser Ser Ile Val Tyr Glu Ala Ala Asp Ala Ile Leu His Thr Pro
    210                 215                 220

Gly Cys Val Pro Cys Val Arg Glu Gly Asn Ala Ser Arg Cys Trp Val
225                 230                 235                 240

Ala Val Thr Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
        275                 280                 285

Gln Leu Phe Thr Phe Ser Pro Arg Arg His Trp Thr Thr Gln Asp Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Ala Ala Leu Val Val Ala Gln
                325                 330                 335

Leu Leu Arg Ile Pro Gln Ala Ile Met Asp Met Ile Ala Gly Ala His
            340                 345                 350

Trp Gly Val Leu Ala Gly Ile Ala Tyr Phe Ser Met Val Gly Asn Trp
        355                 360                 365

Ala Lys Val Leu Val Val Leu Leu Phe Ala Gly Val Asp Ala Glu
    370                 375                 380

Thr His Val Thr Gly Gly Asn Ala Gly Arg Thr Thr Ala Gly Leu Val
385                 390                 395                 400

Gly Leu Leu Thr Pro Gly Ala Lys Gln Asn Ile Gln Leu Ile Asn Thr
                405                 410                 415

Asn Gly Ser Trp His Ile Asn Ser Thr Ala Leu Asn Cys Asn Glu Ser
            420                 425                 430

Leu Asn Thr Gly Trp Leu Ala Gly Leu Phe Tyr Gln His Lys Phe Asn
        435                 440                 445

Ser Ser Gly Cys Pro Glu Arg Leu Ala Ser Cys Arg Arg Leu Thr Asp
    450                 455                 460

Phe Ala Gln Gly Trp Gly Pro Ile Ser Tyr Ala Asn Gly Ser Gly Leu
465                 470                 475                 480
```

-continued

```
Asp Glu Arg Pro Tyr Cys Trp His Tyr Pro Arg Pro Cys Gly Ile
                485                 490                 495

Val Pro Ala Lys Ser Val Cys Gly Pro Val Tyr Cys Phe Thr Pro Ser
                500                 505                 510

Pro Val Val Gly Thr Thr Asp Arg Ser Gly Ala Pro Thr Tyr Ser
            515                 520                 525

Trp Gly Ala Asn Asp Thr Asp Val Phe Val Leu Asn Asn Thr Arg Pro
530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Val Gly Asn
                565                 570                 575

Asn Thr Leu Leu Cys Pro Thr Asp Cys Phe Arg Lys His Pro Glu Ala
                580                 585                 590

Thr Tyr Ser Arg Cys Gly Ser Gly Pro Trp Ile Thr Pro Arg Cys Met
                595                 600                 605

Val Asp Tyr Pro Tyr Arg Leu Trp His Tyr Pro Cys Thr Ile Asn Tyr
            610                 615                 620

Thr Ile Phe Lys Val Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Gln Trp
            660                 665                 670

Gln Val Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
    690                 695                 700

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
                725                 730                 735

Met Met Leu Leu Ile Ser Gln Ala Glu Ala Ala Leu Glu Asn Leu Val
                740                 745                 750

Ile Leu Asn Ala Ala Ser Leu Ala Gly Thr His Gly Leu Val Ser Phe
                755                 760                 765

Leu Val Phe Phe Cys Phe Ala Trp Tyr Leu Lys Gly Arg Trp Val Pro
            770                 775                 780

Gly Ala Val Tyr Ala Leu Tyr Gly Met Trp Pro Leu Leu Leu Leu Leu
785                 790                 795                 800

Leu Ala Leu Pro Gln Arg Ala Tyr Ala Leu Asp Thr Glu Val Ala Ala
                805                 810                 815

Ser Cys Gly Gly Val Val Leu Val Gly Leu Met Ala Leu Thr Leu Ser
                820                 825                 830

Pro Tyr Tyr Lys Arg Tyr Ile Ser Trp Cys Met Trp Trp Leu Gln Tyr
            835                 840                 845

Phe Leu Thr Arg Val Glu Ala Gln Leu His Val Trp Val Pro Pro Leu
        850                 855                 860

Asn Val Arg Gly Gly Arg Asp Ala Val Ile Leu Leu Met Cys Val Val
865                 870                 875                 880

His Pro Thr Leu Val Phe Asp Ile Thr Lys Leu Leu Leu Ala Ile Phe
                885                 890                 895
```

```
Gly Pro Leu Trp Ile Leu Gln Ala Ser Leu Leu Lys Val Pro Tyr Phe
        900                 905                 910

Val Arg Val Gln Gly Leu Leu Arg Ile Cys Ala Leu Ala Arg Lys Ile
        915                 920                 925

Ala Gly Gly His Tyr Val Gln Met Ala Ile Ile Lys Leu Gly Ala Leu
        930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
                965                 970                 975

Ser Arg Met Glu Thr Lys Leu Ile Thr Trp Gly Ala Asp Thr Ala Ala
        980                 985                 990

Cys Gly Asp Ile Ile Asn Gly Leu Pro Val Ser Ala Arg Arg Gly Gln
        995                 1000                1005

Glu Ile Leu Leu Gly Pro Ala Asp Gly Met Val Ser Lys Gly Trp
        1010                1015                1020

Arg Leu Leu Ala Pro Ile Thr Ala Tyr Ala Gln Gln Thr Arg Gly
        1025                1030                1035

Leu Leu Gly Cys Ile Ile Thr Ser Leu Thr Gly Arg Asp Lys Asn
        1040                1045                1050

Gln Val Glu Gly Glu Val Gln Ile Val Ser Thr Ala Thr Gln Thr
        1055                1060                1065

Phe Leu Ala Thr Cys Ile Asn Gly Val Cys Trp Thr Val Tyr His
        1070                1075                1080

Gly Ala Gly Thr Arg Thr Ile Ala Ser Pro Lys Gly Pro Val Ile
        1085                1090                1095

Gln Met Tyr Thr Asn Val Asp Gln Asp Leu Val Gly Trp Pro Ala
        1100                1105                1110

Pro Gln Gly Ser Arg Ser Leu Thr Pro Cys Thr Cys Gly Ser Ser
        1115                1120                1125

Asp Leu Tyr Leu Val Thr Arg His Ala Asp Val Ile Pro Val Arg
        1130                1135                1140

Arg Arg Gly Asp Ser Arg Gly Ser Leu Leu Ser Pro Arg Pro Ile
        1145                1150                1155

Ser Tyr Leu Lys Gly Ser Ser Gly Gly Pro Leu Leu Cys Pro Ala
        1160                1165                1170

Gly His Ala Val Gly Leu Phe Arg Ala Ala Val Cys Thr Arg Gly
        1175                1180                1185

Val Ala Lys Ala Val Asp Phe Ile Pro Val Glu Asn Leu Gly Thr
        1190                1195                1200

Thr Met Arg Ser Pro Val Phe Thr Asp Asn Ser Ser Pro Pro Ala
        1205                1210                1215

Val Pro Gln Ser Phe Gln Val Ala His Leu His Ala Pro Thr Gly
        1220                1225                1230

Ser Gly Lys Ser Thr Lys Val Pro Ala Ala Tyr Ala Ala Gln Gly
        1235                1240                1245

Tyr Lys Val Leu Val Leu Asn Pro Ser Val Ala Ala Thr Leu Gly
        1250                1255                1260

Phe Gly Ala Tyr Met Ser Lys Ala His Gly Val Asp Pro Asn Ile
        1265                1270                1275

Arg Thr Gly Val Arg Thr Ile Thr Thr Gly Ser Pro Ile Thr Tyr
        1280                1285                1290
```

-continued

```
Ser Thr Tyr Gly Lys Phe Leu Ala Asp Gly Gly Cys Ser Gly Gly
    1295                1300                1305

Ala Tyr Asp Ile Ile Ile Cys Asp Glu Cys His Ser Thr Asp Ala
    1310                1315                1320

Thr Ser Ile Leu Gly Ile Gly Thr Val Leu Asp Gln Ala Glu Thr
    1325                1330                1335

Ala Gly Ala Arg Leu Val Val Leu Ala Thr Ala Thr Pro Pro Gly
    1340                1345                1350

Ser Val Thr Val Ser His Pro Asn Ile Glu Glu Val Ala Leu Ser
    1355                1360                1365

Thr Thr Gly Glu Ile Pro Phe Tyr Gly Lys Ala Ile Pro Leu Glu
    1370                1375                1380

Val Ile Lys Gly Gly Arg His Leu Ile Phe Cys His Ser Lys Lys
    1385                1390                1395

Lys Cys Asp Glu Leu Ala Ala Lys Leu Val Ala Leu Gly Ile Asn
    1400                1405                1410

Ala Val Ala Tyr Tyr Arg Gly Leu Asp Val Ser Val Ile Pro Thr
    1415                1420                1425

Ser Gly Asp Val Val Val Ser Thr Asp Ala Leu Met Thr Gly
    1430                1435                1440

Phe Thr Gly Asp Phe Asp Ser Val Ile Asp Cys Asn Thr Cys Val
    1445                1450                1455

Thr Gln Thr Val Asp Phe Ser Leu Asp Pro Thr Phe Thr Ile Glu
    1460                1465                1470

Thr Thr Thr Leu Pro Gln Asp Ala Val Ser Arg Thr Gln Arg Arg
    1475                1480                1485

Gly Arg Thr Gly Arg Gly Lys Pro Gly Ile Tyr Arg Phe Val Ala
    1490                1495                1500

Pro Gly Glu Arg Pro Ser Gly Met Phe Asp Ser Ser Val Leu Cys
    1505                1510                1515

Glu Cys Tyr Asp Ala Gly Cys Ala Trp Tyr Glu Leu Thr Pro Ala
    1520                1525                1530

Glu Thr Thr Val Arg Leu Arg Ala Tyr Met Asn Thr Pro Gly Leu
    1535                1540                1545

Pro Val Cys Gln Asp His Leu Glu Phe Trp Glu Gly Val Phe Thr
    1550                1555                1560

Gly Leu Thr His Ile Asp Ala His Phe Leu Ser Gln Thr Lys Gln
    1565                1570                1575

Ser Gly Glu Asn Phe Pro Tyr Leu Val Ala Tyr Gln Ala Thr Val
    1580                1585                1590

Cys Ala Arg Ala Gln Ala Pro Pro Pro Ser Trp Asp Gln Met Trp
    1595                1600                1605

Lys Cys Leu Ile Arg Leu Lys Pro Thr Leu His Gly Pro Thr Pro
    1610                1615                1620

Leu Leu Tyr Arg Leu Gly Ala Val Gln Asn Glu Val Thr Leu Thr
    1625                1630                1635

His Pro Ile Thr Lys Tyr Ile Met Thr Cys Met Ser Ala Asp Leu
    1640                1645                1650

Glu Val Val Thr Ser Thr Trp Val Leu Val Gly Gly Val Leu Ala
    1655                1660                1665

Ala Leu Ala Ala Tyr Cys Leu Ser Thr Gly Cys Val Val Ile Val
    1670                1675                1680
```

-continued

```
Gly Arg Ile Val Leu Ser Gly Lys Pro Ala Ile Pro Asp Arg
    1685                1690                1695

Glu Val Leu Tyr Gln Glu Phe Asp Glu Met Glu Cys Ser Gln
    1700                1705                1710

His Leu Pro Tyr Ile Glu Gln Gly Met Met Leu Ala Glu Gln Phe
    1715                1720                1725

Lys Gln Lys Ala Leu Gly Leu Leu Gln Thr Ala Ser Arg His Ala
    1730                1735                1740

Glu Val Ile Thr Pro Ala Val Gln Thr Asn Trp Gln Lys Leu Glu
    1745                1750                1755

Val Phe Trp Ala Lys His Met Trp Asn Phe Ile Ser Gly Ile Gln
    1760                1765                1770

Tyr Leu Ala Gly Leu Ser Thr Leu Pro Gly Asn Pro Ala Ile Ala
    1775                1780                1785

Ser Leu Met Ala Phe Thr Ala Ala Val Thr Ser Pro Leu Thr Thr
    1790                1795                1800

Gly Gln Thr Leu Leu Phe Asn Ile Leu Gly Gly Trp Val Ala Ala
    1805                1810                1815

Gln Leu Ala Ala Pro Gly Ala Ala Thr Ala Phe Val Gly Ala Gly
    1820                1825                1830

Leu Ala Gly Ala Ala Ile Gly Ser Val Gly Leu Gly Lys Val Leu
    1835                1840                1845

Val Asp Ile Leu Ala Gly Tyr Gly Ala Gly Val Ala Gly Ala Leu
    1850                1855                1860

Val Ala Phe Lys Ile Met Ser Gly Glu Val Pro Ser Thr Glu Asp
    1865                1870                1875

Leu Val Asn Leu Leu Pro Ala Ile Leu Ser Pro Gly Ala Leu Val
    1880                1885                1890

Val Gly Val Val Cys Ala Ala Ile Leu Arg Arg His Val Gly Pro
    1895                1900                1905

Gly Glu Gly Ala Val Gln Trp Met Asn Arg Leu Ile Ala Phe Ala
    1910                1915                1920

Ser Arg Gly Asn His Val Ser Pro Thr His Tyr Val Pro Glu Ser
    1925                1930                1935

Asp Ala Ala Ala Arg Val Thr Ala Ile Leu Ser Ser Leu Thr Val
    1940                1945                1950

Thr Gln Leu Leu Arg Arg Leu His Gln Trp Ile Ser Ser Glu Cys
    1955                1960                1965

Thr Thr Pro Cys Ser Gly Ser Trp Leu Arg Asp Ile Trp Asp Trp
    1970                1975                1980

Ile Cys Glu Val Leu Ser Asp Phe Lys Thr Trp Leu Lys Ala Lys
    1985                1990                1995

Leu Met Pro Gln Leu Pro Gly Ile Pro Phe Val Ser Cys Gln Arg
    2000                2005                2010

Gly Tyr Arg Gly Val Trp Arg Gly Asp Gly Ile Met His Thr Arg
    2015                2020                2025

Cys His Cys Gly Ala Glu Ile Thr Gly His Val Lys Asn Gly Thr
    2030                2035                2040

Met Arg Ile Val Gly Pro Arg Thr Cys Arg Asn Met Trp Ser Gly
    2045                2050                2055

Thr Phe Pro Ile Asn Ala Tyr Thr Thr Gly Pro Cys Thr Pro Leu
    2060                2065                2070
```

-continued

```
Pro Ala Pro Asn Tyr Lys Phe Ala Leu Trp Arg Val Ser Ala Glu
    2075            2080                2085

Glu Tyr Val Glu Ile Arg Arg Val Gly Asp Phe His Tyr Val Ser
    2090            2095                2100

Gly Met Thr Thr Asp Asn Leu Lys Cys Pro Cys Gln Ile Pro Ser
    2105            2110                2115

Pro Glu Phe Phe Thr Glu Leu Asp Gly Val Arg Leu His Arg Phe
    2120            2125                2130

Ala Pro Pro Cys Lys Pro Leu Leu Arg Glu Val Ser Phe Arg
    2135            2140                2145

Val Gly Leu His Glu Tyr Pro Val Gly Ser Gln Leu Pro Cys Glu
    2150            2155                2160

Pro Glu Pro Asp Val Ala Val Leu Thr Ser Met Leu Thr Asp Pro
    2165            2170                2175

Ser His Ile Thr Ala Glu Ala Ala Gly Arg Arg Leu Ala Arg Gly
    2180            2185                2190

Ser Pro Pro Ser Met Ala Ser Ser Ser Ala Ser Gln Leu Ser Ala
    2195            2200                2205

Pro Ser Leu Lys Ala Thr Cys Thr Ala Asn His Asp Ser Pro Asp
    2210            2215                2220

Ala Glu Leu Ile Glu Ala Asn Leu Leu Trp Arg Gln Glu Met Gly
    2225            2230                2235

Gly Asn Ile Thr Arg Val Glu Ser Glu Asn Lys Val Val Ile Leu
    2240            2245                2250

Asp Ser Phe Asp Pro Leu Val Ala Glu Glu Asp Glu Arg Glu Val
    2255            2260                2265

Ser Val Pro Ala Glu Ile Leu Arg Lys Ser Arg Arg Phe Ala Arg
    2270            2275                2280

Ala Leu Pro Val Trp Ala Arg Pro Asp Tyr Asn Pro Pro Leu Val
    2285            2290                2295

Glu Thr Trp Lys Lys Pro Asp Tyr Glu Pro Pro Val Val His Gly
    2300            2305                2310

Cys Pro Leu Pro Pro Pro Arg Ser Pro Pro Val Pro Pro Pro Arg
    2315            2320                2325

Lys Lys Arg Thr Val Val Leu Thr Glu Ser Thr Leu Ser Thr Ala
    2330            2335                2340

Leu Ala Glu Leu Ala Thr Lys Ser Phe Gly Ser Ser Ser Thr Ser
    2345            2350                2355

Gly Ile Thr Gly Asp Asn Thr Thr Thr Ser Ser Glu Pro Ala Pro
    2360            2365                2370

Ser Gly Cys Pro Pro Asp Ser Asp Val Glu Ser Tyr Ser Ser Met
    2375            2380                2385

Pro Pro Leu Glu Gly Glu Pro Gly Asp Pro Asp Leu Ser Asp Gly
    2390            2395                2400

Ser Trp Ser Thr Val Ser Ser Gly Ala Asp Thr Glu Asp Val Val
    2405            2410                2415

Cys Cys Ser Met Ser Tyr Ser Trp Thr Gly Ala Leu Val Thr Pro
    2420            2425                2430

Cys Ala Ala Glu Glu Gln Lys Leu Pro Ile Asn Ala Leu Ser Asn
    2435            2440                2445

Ser Leu Leu Arg His His Asn Leu Val Tyr Ser Thr Thr Ser Arg
    2450            2455                2460
```

-continued

```
Ser Ala Cys Gln Arg Gln Lys Lys Val Thr Phe Asp Arg Leu Gln
2465                2470                    2475

Val Leu Asp Ser His Tyr Gln Asp Val Leu Lys Glu Val Lys Ala
2480                2485                    2490

Ala Ala Ser Lys Val Lys Ala Asn Leu Leu Ser Val Glu Glu Ala
2495                2500                    2505

Cys Ser Leu Thr Pro Pro His Ser Ala Lys Ser Lys Phe Gly Tyr
2510                2515                    2520

Gly Ala Lys Asp Val Arg Cys His Ala Arg Lys Ala Val Ala His
2525                2530                    2535

Ile Asn Ser Val Trp Lys Asp Leu Leu Glu Asp Ser Val Thr Pro
2540                2545                    2550

Ile Asp Thr Thr Ile Met Ala Lys Asn Glu Val Phe Cys Val Gln
2555                2560                    2565

Pro Glu Lys Gly Gly Arg Lys Pro Ala Arg Leu Ile Val Phe Pro
2570                2575                    2580

Asp Leu Gly Val Arg Val Cys Glu Lys Met Ala Leu Tyr Asp Val
2585                2590                    2595

Val Ser Lys Leu Pro Leu Ala Val Met Gly Ser Ser Tyr Gly Phe
2600                2605                    2610

Gln Tyr Ser Pro Gly Gln Arg Val Glu Phe Leu Val Gln Ala Trp
2615                2620                    2625

Lys Ser Lys Lys Thr Pro Met Gly Phe Ser Tyr Asp Thr Arg Cys
2630                2635                    2640

Phe Asp Ser Thr Val Thr Glu Ser Asp Ile Arg Thr Glu Glu Ala
2645                2650                    2655

Ile Tyr Gln Cys Cys Asp Leu Asp Pro Gln Ala Arg Val Ala Ile
2660                2665                    2670

Lys Ser Leu Thr Glu Arg Leu Tyr Val Gly Gly Pro Leu Thr Asn
2675                2680                    2685

Ser Arg Gly Glu Asn Cys Gly Tyr Arg Arg Cys Arg Ala Ser Gly
2690                2695                    2700

Val Leu Thr Thr Ser Cys Gly Asn Thr Leu Thr Cys Tyr Ile Lys
2705                2710                    2715

Ala Arg Ala Ala Cys Arg Ala Ala Gly Leu Gln Asp Cys Thr Met
2720                2725                    2730

Leu Val Cys Gly Asp Asp Leu Val Val Ile Cys Glu Ser Ala Gly
2735                2740                    2745

Val Gln Glu Asp Ala Ala Ser Leu Arg Ala Phe Thr Glu Ala Met
2750                2755                    2760

Thr Arg Tyr Ser Ala Pro Pro Gly Asp Pro Pro Gln Pro Glu Tyr
2765                2770                    2775

Asp Leu Glu Leu Ile Thr Ser Cys Ser Ser Asn Val Ser Val Ala
2780                2785                    2790

His Asp Gly Ala Gly Lys Arg Val Tyr Tyr Leu Thr Arg Asp Pro
2795                2800                    2805

Thr Thr Pro Leu Ala Arg Ala Ala Trp Glu Thr Ala Arg His Thr
2810                2815                    2820

Pro Val Asn Ser Trp Leu Gly Asn Ile Ile Met Phe Ala Pro Thr
2825                2830                    2835

Leu Trp Ala Arg Met Ile Leu Met Thr His Phe Phe Ser Val Leu
2840                2845                    2850
```

```
Ile Ala Arg Asp Gln Leu Glu  Gln Ala Leu Asn Cys  Glu Ile Tyr
    2855            2860              2865

Gly Ala Cys Tyr Ser Ile Glu  Pro Leu Asp Leu Pro  Pro Ile Ile
    2870            2875              2880

Gln Arg Leu His Gly Leu Ser  Ala Phe Ser Leu His  Ser Tyr Ser
    2885            2890              2895

Pro Gly Glu Ile Asn Arg Val  Ala Ala Cys Leu Arg  Lys Leu Gly
    2900            2905              2910

Val Pro Pro Leu Arg Ala Trp  Arg His Arg Ala Arg  Ser Val Arg
    2915            2920              2925

Ala Arg Leu Leu Ser Arg Gly  Gly Arg Ala Ala Ile  Cys Gly Lys
    2930            2935              2940

Tyr Leu Phe Asn Trp Ala Val  Arg Thr Lys Leu Lys  Leu Thr Pro
    2945            2950              2955

Ile Ala Ala Ala Gly Arg Leu  Asp Leu Ser Gly Trp  Phe Thr Ala
    2960            2965              2970

Gly Tyr Ser Gly Gly Asp Ile  Tyr His Ser Val Ser  His Ala Arg
    2975            2980              2985

Pro Arg Trp Phe Trp Phe Cys  Leu Leu Leu Leu Ala  Ala Gly Val
    2990            2995              3000

Gly Ile Tyr Leu Leu Pro Asn  Arg
    3005            3010
```